(12) United States Patent
Culbertson et al.

(10) Patent No.: US 8,575,102 B2
(45) Date of Patent: Nov. 5, 2013

(54) CONJUGATES HAVING A RELEASABLE LINKAGE

(75) Inventors: Sean M. Culbertson, Gurley, AL (US); Samuel P. McManus, Huntsville, AL (US); Mary J. Bossard, Madison, AL (US)

(73) Assignee: Nektar Therapeutics, San Francisco, CA (US)

(*) Notice: Subject to any disclaimer, the term of this patent is extended or adjusted under 35 U.S.C. 154(b) by 201 days.

(21) Appl. No.: 13/057,042

(22) PCT Filed: Jul. 31, 2009

(86) PCT No.: PCT/US2009/004438
§ 371 (c)(1),
(2), (4) Date: Apr. 19, 2011

(87) PCT Pub. No.: WO2010/014258
PCT Pub. Date: Feb. 4, 2010

(65) Prior Publication Data
US 2011/0190209 A1    Aug. 4, 2011

Related U.S. Application Data

(60) Provisional application No. 61/137,873, filed on Aug. 1, 2008.

(51) Int. Cl.
*A61K 38/36* (2006.01)
*A61K 38/37* (2006.01)
*C07K 14/745* (2006.01)
*C07K 14/755* (2006.01)

(52) U.S. Cl.
USPC .......... 514/13.7; 514/14.1; 530/381; 530/383

(58) Field of Classification Search
None
See application file for complete search history.

(56) References Cited

U.S. PATENT DOCUMENTS

| | | | |
|---|---|---|---|
| 4,424,311 A | 1/1984 | Nagaoka et al. | |
| 4,810,646 A | 3/1989 | Jamas et al. | |
| 4,992,540 A | 2/1991 | Jamas et al. | |
| 5,028,703 A | 7/1991 | Jamas et al. | |
| 5,607,677 A | 3/1997 | Jamas et al. | |
| 5,629,384 A | 5/1997 | Veronese et al. | |
| 5,741,495 A | 4/1998 | Jamas et al. | |
| 5,922,675 A | 7/1999 | Baker et al. | |
| 5,932,462 A | 8/1999 | Harris et al. | |
| 6,362,254 B2 | 3/2002 | Harris et al. | |
| 6,362,276 B1 | 3/2002 | Harris et al. | |
| 7,060,259 B2 | 6/2006 | Bentley et al. | |
| 7,199,223 B2 * | 4/2007 | Bossard et al. | 530/383 |
| 2003/0031647 A1 | 2/2003 | Zahm | |
| 2004/0086991 A1 | 5/2004 | Harris et al. | |
| 2005/0079155 A1 | 4/2005 | Marshall | |
| 2005/0147583 A1 | 7/2005 | Bentley et al. | |
| 2005/0281781 A1 | 12/2005 | Ostroff | |
| 2006/0160948 A1 | 7/2006 | Scheiflinger et al. | |
| 2006/0171920 A1 | 8/2006 | Shechter et al. | |
| 2006/0293499 A1 | 12/2006 | Bentley et al. | |
| 2008/0044438 A1 | 2/2008 | Ostroff et al. | |

FOREIGN PATENT DOCUMENTS

| | | |
|---|---|---|
| WO | WO 86/06096 | 10/1986 |
| WO | WO 94/15625 | 7/1994 |
| WO | WO 96/40749 | 12/1996 |
| WO | WO 2004/075923 | 9/2004 |
| WO | WO 2004/089280 | 10/2004 |
| WO | WO 2006/071801 | 7/2006 |
| WO | WO 2006/138572 | 12/2006 |
| WO | WO 2007/019331 | 2/2007 |
| WO | WO 2007/075534 | 7/2007 |
| WO | WO 2008/011165 | 1/2008 |
| WO | WO 2008/082613 | 7/2008 |
| WO | WO 2008/082669 | 7/2008 |

OTHER PUBLICATIONS

Brown, et al., "An ELISA Test for the Binding of Von Willebrand Antigen to Collagen," Thromb. Res., vol. 43, pp. 303-311, (1986).
Favaloro, "Collagen Binding Assay for von Willebrand Factor (VWF:CBA): Detection of von Willebrands Disease (VWD), and Discrimination of VWD Substypes, Depends on Collagen Source," Thromb. Haemost., vol. 83, pp. 127-135, (2000).
Greenwald, "Drug delivery systems: anticancer prodrugs and their polymeric conjugates," Exp. Opin. on Therap. Pat., vol. 7, No. 6, pp. 601-609, (1997).

(Continued)

*Primary Examiner* — Jeffrey E Russel
(74) *Attorney, Agent, or Firm* — Mark A. Wilson

(57) ABSTRACT

The present invention provides conjugates encompassed by the following structure,

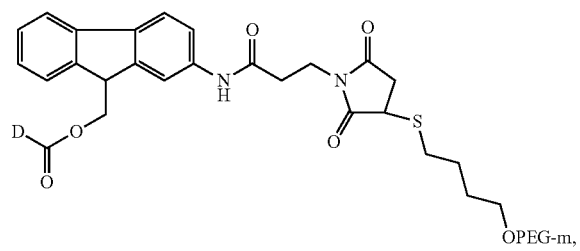

wherein:
D is a residue of an active agent bearing at least one amino group; and
PEG-m is a methoxy end-capped poly(ethylene glycol), and further wherein the active agent is a coagulation factor having a molecular weight of greater than 100 kDa. Methods of making conjugates, and methods for administering conjugates, are also provided.

9 Claims, No Drawings

(56) References Cited

OTHER PUBLICATIONS

Harris, et al., "Effect of Pegylation on Pharmaceuticals," Nat. Rev. Drug Discov., vol. 2, pp. 214-221, (Mar. 2003).
MacFarlane, et al., "A Method for Assaying von Willebrand Factor (Ristocetin Cofactor)," Thromb. Diath. Haemorrh., vol. 34, pp. 306-308, (1975).
Ouchi, et al., "Design of Antitumor Agent-Terminated Poly(Ethylene Glycol) Conjugate as Macromolecular Prodrug," Polym. Preprints, vol. 38, No. 1, pp. 582-583, (1997).
Ouchi, et al., "Synthesis and Antitumor Activity of Poly(Ethylene Glycol)s Linked to 5-Fluorouracil Via a Urethane or Urea Bond," Drug Des. and Discov., vol. 9, pp. 93-105, (1992).
Peleg-Shulman, et al., "Reversible PEGylation: A Novel Technology to Release Native Interferon alpha2 over a Prolonged Time Period," J. Med. Chem., vol. 47, pp. 4897-4904, (2004).
Pitzer, et al., "New Compounds: Fluorene Derivatives as Potential Carcinogens," J. of Pharm. Sci., vol. 57, No. 2, pp. 348-349, (1968).
Shechter, et al., "New Technologies to Prolong Life-time of Peptide and Protein Drugs In Vivo," Intl. J. of Pept. Res. and Therap., vol. 13, Nos. 1-2, (Jun. 2007).
Shechter, et al., "Prolonging the actions of protein and peptide drugs by a novel approach of reversible pegylation," Peptides, Proceedings of the European Peptide Symposium, pp. 48-51, (Sep. 10, 2004).
Shechter, et al., "Reversible PEGylation of peptide YY3-36 prolongs its inhibition of food intake in mice," FEBS Letts., vol. 579, pp. 2439-2444, (2005).
Sims, et al., "A Method for the Estimation of Polyethylene Glycol in Plasma Protein Fractions," Anal. Biochem., vol. 107, pp. 60-63, (1980).
Tsubery, et al., "Prolonging the Action of Protein and Peptide Drugs by a Novel Approach of Reversible Polyethylene Glycol Modification," The J. of Biol. Chem., vol. 279, No. 37, pp. 38118-38124, Issue of Sep. 10, 2004.
Turecek, et al., "Comparative Study on Collagen-Binding Enzyme-Linked Immunosorbent Assay and Ristocetin Cofactor Activity Assays for Detection of Functional Activity of von Willebrand Factor," Sem. in. Thromb. and Hemost., vol. 28, No. 2, pp. 149-160, (2002).
Varadi, et al., "Thrombin generation assay and other universal test for monitoring haemophilia therapy," Haemophilia, vol. 10, (Suppl 2), pp. 17-21, (2004).
Weiss, et al., "Quantitative Assay of a Plasma Factor Deficient in von Willebrand's Disease that is Necessary for Platelet Aggregation," The J. of Clin. Invest., vol. 52, pp. 2708-2716, (Nov. 1973).
Zalipsky, "Synthesis of an End-Group Functionalized Polyethylene Glycol-Lipid Conjugate for Preparation-Grafted Liposomes," Bioconj. Chem., vol. 4, pp. 296-299, (1993).
PCT International Search Report corresponding to PCT Application No. PCT/US2009/004438 date of mailing Oct. 21, 2010.
PCT International Preliminary Report on Patentability corresponding to PCT Application No. PCT/US2009/004438 date of mailing Feb. 10, 2011.
Enzon Pharmaceuticals, Macromolecular Engineering Technologies, 16 pages, (2004).
Nektar™—Transforming Therapeutics, Nektar Molecule Engineering: Polyethylene Glycol and Derivatives for Advanced PEGylation, 24 pages, Catalog—2003, (Jul. 2003).
Nektar™—Transforming Therapeutics, Nektar Advanced PEGylation: Polyethylene Glycol and Derivatives for Advanced PEGylation, 27 pages, Catalog—2004, (Jul. 2004).
Nektar™—Transforming Therapeutics, Nektar Advanced PEGylation: Polyethylene Glycol and Derivatives for Advanced PEGylation, 33 pages, (Catalog 2005-2006).
NOF Corporation, PEG Derivatives, Phospholipid and Drug Delivery Materials for Pharmaceuticals, pp. 1-46, Catalogue 2003—1st, (Jan. 2003).
NOF Corporation, PEG Derivatives, Phospholipid and Drug Delivery Materials for Pharmaceuticals, pp. 1-50, Catalogue 2003—2nd, (Mar. 2004).
NOF Corporation, PEG Derivatives, Phospholipids and Drug Delivery Materials for Pharmaceutical Products and Formulations, 60 pages, Catalogue Ver. 8, (Apr. 2006).
Polypure Products, PEG amines; PEG acids and amino acids; PEG thiols and disulfides; BIOTINS, 5 pages, (Apr. 2004).
Polypure Products, PEG amines; PEG acids and amino acids; PEG thiols and disulfides; BIOTINS, 5 pages, (Apr. 2005).
Quanta Biodesign, Labeling, Derivatization and Crosslinking Reagents for Biological and Related Materials with dPEG™, pp. 1-38, (Mar. 12, 2004).
Quanta Biodesign, Labeling, Modification and Crosslinking Reagents incorporating our unique monodispersed dPEG™ Technology, pp. 1-31, (Nov. 5, 2004).
Quanta Biodesign, Ltd., Leading innovator, producer and provider of monodisperse discrete PEG™ (dPEG™) derivatives, (Product Catalog), pp. 1-51, (Updated: Jul. 18, 2005).
Quanta Biodesign, Ltd., Leading innovator, producer and provider of monodisperse discrete PEG™ (dPEG™) derivatives, (Product Catalog), pp. 1-51, (Updated: Nov. 17, 2005).
Shearwater Polymers, Inc., Polyethylene Glycol and Derivatives, 50 pages, (Catalog—Mar. 1995).
Shearwater Polymers, Inc., Polyethylene Glycol and Derivatives, 55 pages, (Catalog—Jul. 1997).
Shearwater Polymers, Inc., Polyethylene Glycol and Derivatives: Functionalized Biocompatible Polymers for Research and Pharmaceuticals, pp. 1-50, (Catalog—Jan. 2000).
Shearwater Corporation, Polyethylene Glycol and Derivatives for Biomedical Applications, 20 pages, (Catalog—Jul. 2001).

* cited by examiner

CONJUGATES HAVING A RELEASABLE LINKAGE

CROSS-REFERENCE TO RELATED APPLICATIONS

This application is a 35 U.S.C. §371 application of International Application No. PCT/US2009/004438, filed 31 Jul. 2009, designating the United States, which claims the benefit of priority under 35 U.S.C. §119(e) to U.S. Provisional Patent Application Ser. No. 61/137,873, filed 1 Aug. 2008, both of which are incorporated herein by reference in their entireties.

BACKGROUND OF THE INVENTION

The present invention relates generally to polymer-active agent conjugates having a releasable linkage to thereby release the active agent. In addition, the invention relates to, among other things, methods for synthesizing the conjugates, methods for purifying the conjugates, and so on.

BACKGROUND OF THE INVENTION

Scientists and clinicians face a number of challenges in their attempts to develop active agents into forms suited for delivery to a patient. Active agents that are polypeptides, for example, are often delivered via injection rather than orally. In this way, the polypeptide is introduced into the systemic circulation without exposure to the proteolytic environment of the stomach. Injection of polypeptides, however, has several drawbacks. For example, many polypeptides have a relatively short half-life, thereby necessitating repeated injections, which are often inconvenient and painful. Moreover, some polypeptides can elicit one or more immune responses with the consequence that the patient's immune system attempts to destroy or otherwise neutralize the immunogenic polypeptide. Of course, once the polypeptide has been destroyed or otherwise neutralized, the polypeptide cannot exert its intended pharmacodynamic activity. Thus, delivery of active agents such as polypeptides is often problematic even when these agents are administered by injection.

Some success has been achieved in addressing the problems of delivering active agents via injection. For example, conjugating the active agent to a water-soluble polymer has resulted in polymer-active agent conjugates having reduced immunogenicity and antigenicity. In addition, these polymer-active agent conjugates often have greatly increased half-lives compared to their unconjugated counterparts as a result of decreased clearance through the kidney and/or decreased enzymatic degradation in the systemic circulation. As a result of having a greater half-life, the polymer-active agent conjugate requires less frequent dosing, which in turn reduces the overall number of painful injections and inconvenient visits with a health care professional. Moreover, active agents that were only marginally soluble demonstrate a significant increase in water solubility when conjugated to a water-soluble polymer.

Due to its documented safety as well as its approval by the FDA for both topical and internal use, polyethylene glycol has been conjugated to active agents. When an active agent is conjugated to a polymer of polyethylene glycol or "PEG," the conjugated active agent is conventionally referred to as "PEGylated." The commercial success of PEGylated active agents such as PEGASYS® PEGylated interferon alpha-2a (Hoffmann-La Roche, Nutley, N.J.), PEG-INTRON® PEGylated interferon alpha-2b (Schering Corp., Kennilworth, N.J.), and NEULASTA™ PEG-filgrastim (Amgen Inc., Thousand Oaks, Calif.) demonstrates that administration of a conjugated form of an active agent can have significant advantages over the unconjugated counterpart. Small molecules such as distearoylphosphatidylethanolamine (Zalipsky (1993) *Bioconjug. Chem.* 4(4):296-299) and fluorouracil (Ouchi et al. (1992) *Drug Des. Discov.* 9(1):93-105) have also been PEGylated. Harris et al. have provided a review of the effects of PEGylation on pharmaceuticals. Harris et al. (2003) *Nat. Rev. Drug Discov.* 2(3):214-221.

Despite these successes, conjugation of a polymer to an active agent to result in a commercially relevant drug is often challenging. For example, conjugation can result in the polymer being attached at or near a site on the active agent that is necessary for pharmacologic activity (e.g., at or near a binding site). Such conjugates may therefore have unacceptably low activity due to, for example, the steric effects introduced by the polymer. Attempts to remedy conjugates having unacceptably low activity can be frustrated when the active agent has few or no other sites suited for attachment to a polymer. Thus, additional PEGylation alternatives have been desired.

One suggested approach for solving this and other problems is "reversible PEGylation" wherein the native active agent (or a moiety having increased activity compared to the PEGylated active agent) is released. For example, reversible PEGylation has been disclosed in the field of cancer chemotherapies. See Greenwald (1997) *Exp. Opin. Ther. Patents* 7(6):601-609. U.S. Patent Application Publication No. 2005/0079155 describes conjugates using reversible linkages. As described in this publication, reversible linkages can be effected through the use of an enzyme substrate moiety. It has been pointed out, however, that approaches relying on enzymatic activity are dependent on the availability of enzymes. See Peleg-Schulman (2004) *J. Med. Chem.* 47:4897-4904. Patient variability around the amount and activity of these enzymes can introduce inconsistent performance of the conjugate among different populations. Thus, additional approaches that do not rely on enzymatic processes for degradation have been described as being desirable.

Another approach for reversible PEGylation is described in U.S. Pat. No. 7,060,259, which describes (among other things) water-soluble prodrugs in which a biologically active agent is linked to a water-soluble non-immunogenic polymer by a hydrolysable carbamate bond. As described therein, the biologically active agent can be readily released by the hydrolysis of the carbmate bond in vivo without the need for adding enzymes or catalytic materials.

Another approach for reversible PEGylation is described in Peleg-Schulman (2004) *J. Med. Chem.* 47:4897-4904, WO 2004/089280 and U.S. Patent Application Publication No. 2006/0171920. Although this approach has been applied to a limited number of active agents, these references ignore other active agents for which reversible PEGylation would be particularly suited.

In the area of bleeding disorders, von Willebrand's disease is a relatively common disorder that can be treated with replacement therapy. In von Willebrand's disease, the body does not produce sufficient von Willebrand factor. Hemophilia is a group of hereditary genetic disorders that impair the body's ability to control blood clotting or coagulation. In hemophilia A, clotting factor VIII is deficient. In Hemophilia B, factor IX is deficient. In hemophilia C, factor XI is deficient. In one approach of replacement therapy, these factors are periodically administered via injection to the patients lacking them. Due to the short half-life of these proteins, it would be advantageous to increase the in vivo half-life of these proteins by, for example, reversible PEGylation. Thus, the present invention seeks to solve these and other needs in the art.

SUMMARY OF THE INVENTION

In one or more embodiments of the invention, a conjugate of the following formula is provided:

(X)$_n$-D wherein:

D is a residue of an active agent bearing at least one functional group selected from the group consisting of amino, carboxyl, phosphate, hydroxyl, and mercapto, and X is a radical selected from the group consisting of the group of radicals having the formulas (i) to (iv):

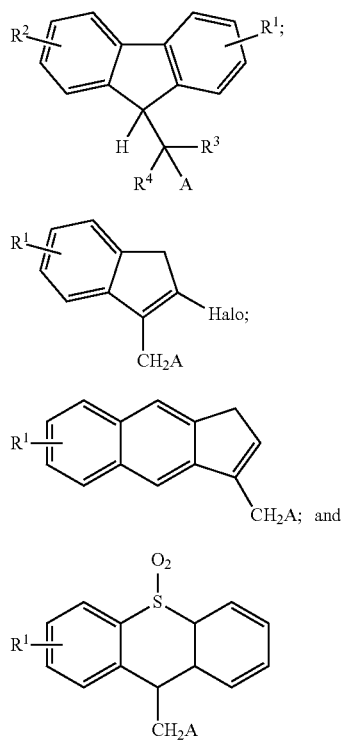

formula (i)

formula (ii)

formula (iii)

formula (iv)

wherein:

R$^1$ is a radical containing a water soluble, non-peptidic polymer moiety;

R$^2$ is selected from the group consisting of hydrogen, alkyl, substituted alkyl, alkoxy, alkoxyalkyl, aryl, alkaryl, aralkyl, substituted aryl, heteroaryl, halogen, nitro, —SO$_3$H, —SO$_2$NHR, amino, ammonium, substituted ammonium, carboxyl, PO$_3$H$_2$, and OPO$_3$H$_2$;

R is selected from the group consisting of hydrogen, alkyl, aryl, and heteroaryl;

R$^3$ is selected from the group consisting of hydrogen, alkyl, aryl, and heteroaryl;

R$^4$ is selected from the group consisting of hydrogen, alkyl, aryl, and heteroaryl;

A is a covalent bond when the radical is linked to a carboxyl, phosphate or mercapto group of the D, or A is OCO— when the radical is linked to an amino or hydroxyl group of the active agent; and (n) is an integer of one or greater, and pharmaceutically acceptable salts thereof.

In another embodiment of the above formulae, R$^1$ is a radical containing a polyethylene glycol (PEG) moiety.

In one or more embodiments of the invention, methods for preparing conjugates are provided.

In one or more embodiments of the invention, pharmaceutical preparations comprising the conjugates are provided.

In one or more embodiments of the invention, methods for administering the conjugates are provided.

DETAILED DESCRIPTION OF THE INVENTION

Before describing the present invention in detail, it is to be understood that this invention is not limited to the particular polymers, synthetic techniques, active agents, and the like, as such may vary.

It must be noted that, as used in this specification and the claims, the singular forms "a," "an," and "the" include plural referents unless the context clearly dictates otherwise. Thus, for example, reference to a "polymer" includes a single polymer as well as two or more of the same or different polymers, reference to a "conjugate" refers to a single conjugate as well as two or more of the same or different conjugates, reference to an "excipient" includes a single excipient as well as two or more of the same or different excipients, and the like.

In describing and claiming the present invention, the following terminology will be used in accordance with the definitions described below.

"PEG," "polyethylene glycol" and "poly(ethylene glycol)" as used herein, are meant to encompass any water-soluble poly(ethylene oxide). Typically, PEGs for use in accordance with the invention comprise the following structure "—O(CH$_2$CH$_2$O)$_m$—" where (m) is 2 to 4000. As used herein, PEG also includes "—CH$_2$CH$_2$—O(CH$_2$CH$_2$O)$_m$—CH$_2$CH$_2$—" and "—(CH$_2$CH$_2$O)$_n$—," depending upon whether or not the terminal oxygens have been displaced. When the PEG further comprises a spacer moiety (to be described in greater detail below), the atoms comprising the spacer moiety, when covalently attached to a water-soluble polymer segment, do not result in the formation of an oxygen-oxygen bond (i.e., an "—O—O—" or peroxide linkage). Throughout the specification and claims, it should be remembered that the term "PEG" includes structures having various terminal or "end capping" groups and so forth. The term "PEG" also means a polymer that contains a majority, that is to say, greater than 50%, of —CH$_2$CH$_2$O— monomeric subunits. With respect to specific forms, the PEG can take any number of a variety of molecular weights, as well as structures or geometries such as "branched," "linear," "forked," "multifunctional," and the like, to be described in greater detail below.

The terms "end-capped" or "terminally capped" are interchangeably used herein to refer to a terminal or endpoint of a polymer having an end-capping moiety. Typically, although not necessarily, the end-capping moiety comprises a hydroxy or C$_{1-20}$ alkoxy group. Thus, examples of end-capping moieties include alkoxy (e.g., methoxy, ethoxy and benzyloxy), as well as aryl, heteroaryl, cyclo, heterocyclo, and the like. In addition, saturated, unsaturated, substituted and unsubstituted forms of each of the foregoing are envisioned. Moreover, the end-capping group can also be a silane. The end-capping group can also advantageously comprise a detectable label. When the polymer has an end-capping group comprising a detectable label, the amount or location of the polymer and/or the moiety (e.g., active agent) of interest to which the polymer is coupled, can be determined by using a suitable detector. Such labels include, without limitation, fluorescers, chemiluminescers, moieties used in enzyme labeling, colorimetric moieties (e.g., dyes), metal ions, radioactive moieties, and the like. Suitable detectors include photometers, films, spectrometers, and the like.

The term "targeting moiety" is used herein to refer to a molecular structure that helps the conjugates of the invention to localize to a targeting area, e.g., help enter a cell, or bind a receptor. Preferably, the targeting moiety comprises of vitamin, antibody, antigen, receptor, DNA, RNA, sialyl Lewis X antigen, hyaluronic acid, sugars, cell specific lectins, steroid or steroid derivative, RGD peptide, ligand for a cell surface receptor, serum component, or combinatorial molecule directed against various intra- or extracellular receptors. The targeting moiety may also comprise a lipid or a phospholipid. Exemplary phospholipids include, without limitation, phosphatidylcholines, phospatidylserine, phospatidylinositol, phospatidylglycerol, and phospatidylethanolamine. These lipids may be in the form of micelles or liposomes and the like. The targeting moiety may further comprise a detectable label or alternately a detectable label may serve as a targeting moiety. When the conjugate has a targeting group comprising a detectable label, the amount and/or distribution/location of the polymer and/or the moiety (e.g., active agent) to which the polymer is coupled can be determined by using a suitable detector. Such labels include, without limitation, fluorescers, chemiluminescers, moieties used in enzyme labeling, colorimetric (e.g., dyes), metal ions, radioactive moieties, gold particles, quantum dots, and the like.

"Non-naturally occurring" with respect to a polymer or water-soluble polymer means a polymer that in its entirety is not found in nature. A non-naturally occurring polymer or water-soluble polymer may, however, contain one or more subunits or portions of a subunit that are naturally occurring, so long as the overall polymer structure is not found in nature.

The term "water-soluble polymer" is any polymer that is soluble in water at room temperature. Typically, a water-soluble polymer will transmit at least about 75%, more preferably at least about 95% of light, transmitted by the same solution after filtering. On a weight basis, a water-soluble polymer will preferably be at least about 35% (by weight) soluble in water, more preferably at least about 50% (by weight) soluble in water, still more preferably about 70% (by weight) soluble in water, and still more preferably about 85% (by weight) soluble in water. It is still more preferred, however, that the water-soluble polymer is about 95% (by weight) soluble in water and most preferred that the water-soluble polymer is completely soluble in water.

Molecular weight in the context of a water-soluble polymer of the invention, such as PEG, can be expressed as either a number average molecular weight or a weight average molecular weight. Unless otherwise indicated, all references to molecular weight herein refer to the weight average molecular weight. Both molecular weight determinations, number average and weight average, can be measured using gel permeation chromatography or other liquid chromatography techniques. Other methods for measuring molecular weight values can also be used, such as the use of end-group analysis or the measurement of colligative properties (e.g., freezing-point depression, boiling-point elevation, and osmotic pressure) to determine number average molecular weight or the use of light scattering techniques, ultracentrifugation or viscometry to determine weight average molecular weight. The polymers of the invention are typically polydisperse (i.e., number average molecular weight and weight average molecular weight of the polymers are not equal), possessing low polydispersity values of preferably less than about 1.2, more preferably less than about 1.15, still more preferably less than about 1.10, yet still more preferably less than about 1.05, and most preferably less than about 1.03.

As used herein, the term "carboxylic acid" is a moiety having a

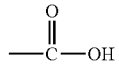

functional group [also represented as a "—COOH" or —C(O)OH], as well as moieties that are derivatives of a carboxylic acid, such derivatives including, for example, protected carboxylic acids. Thus, unless the context clearly dictates otherwise, the term carboxylic acid includes not only the acid form, but corresponding esters and protected forms as well. With regard to protecting groups suited for a carboxylic acid and any other functional group described herein, reference is made to Greene et al., "PROTECTIVE GROUPS IN ORGANIC SYNTHESIS" 3$^{rd}$ Edition, John Wiley and Sons, Inc., New York, 1999.

The term "reactive" or "activated" when used in conjunction with a particular functional group, refers to a reactive functional group that reacts readily with an electrophile or a nucleophile on another molecule. This is in contrast to those groups that require strong catalysts or highly impractical reaction conditions in order to react (i.e., a "nonreactive" or "inert" group).

The terms "protected" or "protecting group" or "protective group" refer to the presence of a moiety (i.e., the protecting group) that prevents or blocks reaction of a particular chemically reactive functional group in a molecule under certain reaction conditions. The protecting group will vary depending upon the type of chemically reactive functional group being protected as well as the reaction conditions to be employed and the presence of additional reactive or protecting groups in the molecule, if any. Protecting groups known in the art can be found in Greene et al., supra.

As used herein, the term "functional group" or any synonym thereof is meant to encompass protected forms thereof.

The terms "spacer" or "spacer moiety" are used herein to refer to an atom or a collection of atoms optionally used to link one moiety to another, such as a water-soluble polymer segment to an aromatic-containing moiety. The spacer moieties of the invention may be hydrolytically stable or may include one or more physiologically hydrolyzable or enzymatically releasable linkages.

An "organic radical" as used herein includes, for example, alkyl, substituted alkyl, alkenyl, substituted alkenyl, alkynyl, substituted alkynyl, aryl and substituted aryl.

"Alkyl" refers to a hydrocarbon, typically ranging from about 1 to 20 atoms in length. Such hydrocarbons are preferably but not necessarily saturated and may be branched or straight chain, although typically straight chain is preferred. Exemplary alkyl groups include ethyl, propyl, butyl, pentyl, 2-methylbutyl, 2-ethylpropyl, 3-methylpentyl, and the like. As used herein, "alkyl" includes cycloalkyl when three or more carbon atoms are referenced and lower alkyl.

"Lower alkyl" refers to an alkyl group containing from 1 to 6 carbon atoms, and may be straight chain or branched, as exemplified by methyl, ethyl, n-butyl, iso-butyl, and tert-butyl.

"Cycloalkyl" refers to a saturated or unsaturated cyclic hydrocarbon chain, including bridged, fused, or Spiro cyclic compounds, preferably made up of 3 to about 12 carbon atoms, more preferably 3 to about 8.

"Non-interfering substituents" are those groups that, when present in a molecule, are typically non-reactive with other functional groups contained within the molecule.

The term "substituted" as in, for example, "substituted alkyl," refers to a moiety (e.g., an alkyl group) substituted with one or more non-interfering substituents, such as, but not limited to: $C_3$-$C_8$ cycloalkyl, e.g., cyclopropyl, cyclobutyl, and the like; halo, e.g., fluoro, chloro, bromo, and iodo; cyano; alkoxy, lower phenyl (e.g., –2 substituted phenyl); substituted phenyl; and the like, for one or more hydrogen atoms. "Substituted aryl" is aryl having one or more non-interfering groups as a substituent. For substitutions on a phenyl ring, the substituents may be in any orientation (i.e., ortho, meta, or para). "Substituted ammonium" is ammonium having one or more non-interfering groups (e.g., an organic radical) as a substituent.

"Alkoxy" refers to an —O—R group, wherein R is alkyl or substituted alkyl, preferably $C_1$-$C_{20}$ alkyl (e.g., methoxy, ethoxy, propyloxy, etc.), more preferably $C_1$-$C_7$ alkyl.

As used herein, "alkenyl" refers to a branched or unbranched hydrocarbon group of 1 to 15 atoms in length, containing at least one double bond, such as ethenyl, n-propenyl, isopropenyl, n-butenyl, isobutenyl, octenyl, decenyl, tetradecenyl, and the like.

The term "alkynyl" as used herein refers to a branched or unbranched hydrocarbon group of 2 to 15 atoms in length, containing at least one triple bond, ethynyl, n-butynyl, isopentynyl, octynyl, decynyl, and so forth.

"Aryl" means one or more aromatic rings, each of 5 or 6 core carbon atoms. Aryl includes multiple aryl rings that may be fused, as in naphthyl or unfused, as in biphenyl. Aryl rings may also be fused or unfused with one or more cyclic hydrocarbon, heteroaryl, or heterocyclic rings. As used herein, "aryl" includes heteroaryl. An aromatic moiety (e.g., $Ar^1$, $Ar^2$, and so forth), means a structure containing aryl.

"Heteroaryl" is an aryl group containing from one to four heteroatoms, preferably N, O, or S, or a combination thereof. Heteroaryl rings may also be fused with one or more cyclic hydrocarbon, heterocyclic, aryl, or heteroaryl rings.

"Heterocycle" or "heterocyclic" means one or more rings of 5-12 atoms, preferably 5-7 atoms, with or without unsaturation or aromatic character and having at least one ring atom which is not a carbon. Preferred heteroatoms include sulfur, oxygen, and nitrogen.

"Substituted heteroaryl" is heteroaryl having one or more non-interfering groups as substituents.

"Substituted heterocycle" is a heterocycle having one or more side chains formed from non-interfering substituents.

"Electrophile" refers to an ion or atom or collection of atoms that may be ionic, having an electrophilic center, i.e., a center that is electron seeking, capable of reacting with a nucleophile.

"Nucleophile" refers to an ion or atom or collection of atoms that may be ionic having a nucleophilic center, i.e., a center that is seeking an electrophilic center or with an electrophile.

A "physiologically cleavable" or "hydrolyzable" bond is a relatively weak bond that reacts with water (i.e., is hydrolyzed) under physiological conditions. The tendency of a bond to hydrolyze in water will depend not only on the general type of linkage connecting two central atoms but also on the substituents attached to these central atoms. Appropriate hydrolytically unstable or weak linkages include, but are not limited to, carboxylate ester, phosphate ester, anhydrides, acetals, ketals, acyloxyalkyl ether, imines, ortho esters, peptides and oligonucleotides.

A "releasable linkage" includes, but is not limited to, a physiologically cleavable bond, a hydrolyzable bond, and an enzymatically releasable linkage. Thus, a "releasable linkage" is a linkage that may undergo either hydrolysis or cleavage by some other mechanism (e.g., enzyme-catalyzed, acid-catalyzed, base-catalyzed, and so forth) under physiological conditions. For example, a "releaseable linkage" can involve an elimination reaction that has a base abstraction of a proton, (e.g., an ionizable hydrogen atom, $H_\alpha$), as the driving force.

An "enzymatically releasable linkage" means a linkage that is subject to degradation by one or more enzymes.

A "hydrolytically stable" linkage or bond refers to a chemical bond, typically a covalent bond that is substantially stable in water, that is to say, does not undergo hydrolysis under physiological conditions to any appreciable extent over an extended period of time. Examples of hydrolytically stable linkages include but are not limited to the following: carbon-carbon bonds (e.g., in aliphatic chains), ethers, amides, urethanes (carbamates), and the like. Generally, a hydrolytically stable linkage is one that exhibits a rate of hydrolysis of less than about 1-2% per day under physiological conditions. Hydrolysis rates of representative chemical bonds can be found in most standard chemistry textbooks. It must be pointed out that some linkages can be hydrolytically stable or hydrolyzable, depending upon (for example) adjacent and neighboring atoms and ambient conditions. One of ordinary skill in the art can determine whether a given linkage or bond is hydrolytically stable or hydrolyzable in a given context by, for example, placing a linkage-containing molecule of interest under conditions of interest and testing for evidence of hydrolysis (e.g., the presence and amount of two molecules resulting from the cleavage of a single molecule). Other approaches known to those of ordinary skill in the art for determining whether a given linkage or bond is hydrolytically stable or hydrolyzable can also be used.

The terms "active agent," "biologically active agent" and "pharmacologically active agent" are used interchangeably herein and are defined to include any agent, drug, compound, composition of matter, or mixture that provides some pharmacologic, often beneficial, effect that can be demonstrated in vivo or in vitro. This includes foods, food supplements, nutrients, nutriceuticals, drugs, proteins, vaccines, antibodies, vitamins, and other beneficial agents. As used herein, these terms further include any physiologically or pharmacologically active substance that produces a localized or systemic effect in a patient.

"Pharmaceutically acceptable excipient" or "pharmaceutically acceptable carrier" refers to an excipient that can be included in the compositions of the invention and that causes no significant adverse toxicological effects to the patient.

"Pharmacologically effective amount," "physiologically effective amount," and "therapeutically effective amount" are used interchangeably herein to mean the amount of a polymer-active agent conjugate—typically present in a pharmaceutical preparation—that is needed to provide a desired level of active agent and/or conjugate in the bloodstream or in a target tissue. The exact amount will depend upon numerous factors, e.g., the particular active agent, the components and physical characteristics of the pharmaceutical preparation, intended patient population, patient considerations, and the like, and can readily be determined by one of ordinary skill in the art, based upon the information provided herein and available in the relevant literature.

"Multifunctional" in the context of a polymer of the invention means a polymer having 3 or more functional groups contained therein, where the functional groups may be the same or different. Multifunctional polymers of the invention will typically contain from about 3-100 functional groups, or from 3-50 functional groups, or from 3-25 functional groups, or from 3-15 functional groups, or from 3 to 10 functional groups, or will contain 3, 4, 5, 6, 7, 8, 9 or 10 functional groups within the polymer. A "difunctional" polymer means a polymer having two functional groups contained therein, either the same (i.e., homodifunctional) or different (i.e., heterodifunctional).

"Branched," in reference to the geometry or overall structure of a polymer, refers to a polymer having 2 or more polymer "arms." A branched polymer may possess 2 polymer arms, 3 polymer arms, 4 polymer arms, 6 polymer arms, 8 polymer arms or more. One particular type of highly branched polymer is a dendritic polymer or dendrimer, which, for the purposes of the invention, is considered to possess a structure distinct from that of a branched polymer.

A "dendrimer" or dendritic polymer is a globular, size monodisperse polymer in which all bonds emerge radially from a central focal point or core with a regular branching pattern and with repeat units that each contributes a branch point. Dendrimers exhibit certain dendritic state properties such as core encapsulation, making them unique from other types of polymers.

A basic or acidic reactant described herein includes neutral, charged, and any corresponding salt forms thereof.

The term "patient," refers to a living organism suffering from or prone to a condition that can be prevented or treated by administration of a conjugate as provided herein, and includes both humans and animals.

As used herein, "drug release rate" means a rate (stated as a half-life) in which half of the total amount of polymer-active agent conjugates in a system will cleave into the active agent and a polymeric residue.

"Optional" and "optionally" mean that the subsequently described circumstance may or may not occur, so that the description includes instances where the circumstance occurs and instances where it does not.

As used herein, the "halo" designator (e.g., fluoro, chloro, iodo, bromo, and so forth) is generally used when the halogen is attached to a molecule, while the suffix "ide" (e.g., fluoride, chloride, iodide, bromide, and so forth) is used when the halogen exists in its independent ionic form (e.g., such as when a leaving group leaves a molecule).

In the context of the present discussion, it should be recognized that the definition of a variable provided with respect to one structure or formula is applicable to the same variable repeated in a different structure, unless the context dictates otherwise.

As previously stated, the present invention comprises (among other things) conjugates having a releasable linkage.

Before describing exemplary conjugates of the invention, embodiments of a water-soluble polymer and a functional group capable of reacting with an amino group of an active agent to form a releasable linkage, such as a carbamate linkage will be discussed.

With respect to a given water-soluble polymer, each water-soluble polymer (e.g., POLY, POLY$^1$ and POLY$^2$) can comprise any polymer so long as the polymer is water-soluble and non-peptidic. Although preferably a poly(ethylene glycol), a water-soluble polymer for use herein can be, for example, other water-soluble polymers such as other poly(alkylene glycols), such as polypropylene glycol ("PPG"), copolymers of ethylene glycol and propylene glycol and the like, poly (olefinic alcohol), poly(vinylpyrrolidone), poly(hydroxyalkylmethacrylamide), poly(hydroxyalkylmethacrylate), poly(saccharides), poly(α-hydroxy acid), poly(vinyl alcohol), polyphosphazene, polyoxazoline, poly(N-acryloylmorpholine), such as described in U.S. Pat. No. 5,629,384. The water soluble polymer can be a homopolymer, copolymer, terpolymer, nonrandom block polymer, and random block polymer of any of the foregoing. In addition, a water-soluble polymer can be linear, but can also be in other forms (e.g., branched, forked, and the like) as will be described in further detail below. In the context of being present within an overall structure, a water-soluble polymer has from 1 to about 300 termini.

In instances where the polymeric reagent comprises two or more water-soluble polymers, each water-soluble polymer in the overall structure can be the same or different. It is preferred, however, that all water-soluble polymers in the overall structure are of the same type. For example, it is preferred that all water-soluble polymers within a given structure are each a poly(ethylene glycol).

Although the weight-average molecular weight of any individual water-soluble polymer can vary, the weight-average molecular weight of any given water-soluble polymer will typically be in the following range: 100 Daltons to about 150,000 Daltons. Exemplary ranges, however, include weight-average molecular weights in the following ranges: about 880 Daltons to about 5,000 Daltons; in the range of greater than 5,000 Daltons to about 100,000 Daltons; in the range of from about 6,000 Daltons to about 90,000 Daltons; in the range of from about 10,000 Daltons to about 85,000 Daltons; in the range of greater than 10,000 Daltons to about 85,000 Daltons; in the range of from about 20,000 Daltons to about 85,000 Daltons; in the range of from about 53,000 Daltons to about 85,000 Daltons; in the range of from about 25,000 Daltons to about 120,000 Daltons; in the range of from about 29,000 Daltons to about 120,000 Daltons; in the range of from about 35,000 Daltons to about 120,000 Daltons; in the range of about 880 Daltons to about 60,000 Daltons; in the range of about 440 Daltons to about 40,000 Daltons; in the range of about 440 Daltons to about 30,000 Daltons; and in the range of from about 40,000 Daltons to about 120,000 Daltons. For any given water-soluble polymer, PEGs having a molecular weight in one or more of these ranges are preferred.

Exemplary weight-average molecular weights for the water-soluble polymer include about 100 Daltons, about 200 Daltons, about 300 Daltons, about 400 Daltons, about 440 Daltons, about 500 Daltons, about 600 Daltons, about 700 Daltons, about 750 Daltons, about 800 Daltons, about 900 Daltons, about 1,000 Daltons, about 1,500 Daltons, about 2,000 Daltons, about 2,200 Daltons, about 2,500 Daltons, about 3,000 Daltons, about 4,000 Daltons, about 4,400 Daltons, about 4,500 Daltons, about 5,000 Daltons, about 5,500 Daltons, about 6,000 Daltons, about 7,000 Daltons, about 7,500 Daltons, about 8,000 Daltons, about 9,000 Daltons, about 10,000 Daltons, about 11,000 Daltons, about 12,000 Daltons, about 13,000 Daltons, about 14,000 Daltons, about 15,000 Daltons, about 16,000 Daltons, about 17,000 Daltons, about 18,000 Daltons, about 19,000 Daltons, about 20,000 Daltons, about 22,500 Daltons, about 25,000 Daltons, about 30,000 Daltons, about 35,000 Daltons, about 40,000 Daltons, about 45,000 Daltons, about 50,000 Daltons, about 55,000 Daltons, about 60,000 Daltons, about 65,000 Daltons, about 70,000 Daltons, and about 75,000 Daltons. Branched versions of the water-soluble polymer (e.g., a branched 40,000 Dalton water-soluble polymer comprised of two 20,000 Dalton polymers) having a total weight average molecular weight of any of the foregoing can also be used.

The polymeric reagent will comprise a water-soluble polymer having a size in the range suited for the desired rate of release of the conjugate formed therefrom. For example, a conjugate having a relatively long release rate can be prepared from a polymeric reagent having a size suited for (a) extended circulation prior to degradation of the conjugate, and (b) moderately rapid in vivo clearance of the water-soluble polymer remainder upon degradation of the conjugate. Likewise, when the conjugate has a relatively fast release rate, then the polymeric reagent would typically have a lower molecular weight.

When a PEG is used as the water-soluble polymer in the polymeric reagent, the PEG typically comprises a number of ($OCH_2CH_2$) monomers [or ($CH_2CH_2O$) monomers, depending on how the PEG is defined]. As used throughout the description, the number of repeating units is identified by the subscript "n" in "($OCH_2CH_2$)$_n$." Thus, the value of (n) typically falls within one or more of the following ranges: from 2 to about 3400, from about 4 to about 1500, from about 100 to about 2300, from about 100 to about 2270, from about 136 to about 2050, from about 225 to about 1930, from about 450 to about 1930, from about 1200 to about 1930, from about 568 to about 2727, from about 660 to about 2730, from about 795 to about 2730, from about 795 to about 2730, from about 909 to about 2730, and from about 1,200 to about 1,900. For any given polymer in which the molecular weight is known, it is possible to determine the number of repeating units (i.e., "n") by dividing the molecular weight of the polymer by the molecular weight of the repeating monomer.

Each water-soluble polymer is typically biocompatible and non-immunogenic. With respect to biocompatibility, a substance is considered biocompatible if the beneficial effects associated with use of the substance alone or with another substance (e.g., an active agent) in connection with living tissues (e.g., administration to a patient) outweighs any deleterious effects as evaluated by a clinician, e.g., a physician. With respect to non-immunogenicity, a substance is considered non-immunogenic if use of the substance alone or with another substance in connection with living tissues does not produce an immune response (e.g., the formation of antibodies) or, if an immune response is produced, that such a response is not deemed clinically significant or important as evaluated by a clinician. It is particularly preferred that the water-soluble polymers, described herein as well as conjugates of active agents and the polymers are biocompatible and non-immunogenic.

In one useful form, free or nonbound PEG is a linear polymer terminated at each end with hydroxyl groups:

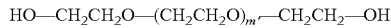

wherein (m') typically ranges from zero to about 4,000, preferably from about 20 to about 1,000.

The above polymer, alpha-, omega-dihydroxylpoly(ethylene glycol), can be represented in brief form as HO-PEG-OH where it is understood that the -PEG- symbol can represent the following structural unit:

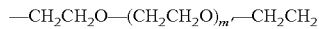

where (m') is as defined as above.

Another type of free or nonbound PEG useful in the present invention is methoxy-PEG-OH, or mPEG in brief, in which one terminus is the relatively inert methoxy group, while the other terminus is a hydroxyl group. The structure of mPEG is given below.

where (m') is as described above.

Multi-armed or branched PEG molecules, such as those described in U.S. Pat. No. 5,932,462, can also be used as the PEG polymer. For example, PEG can have the structure:

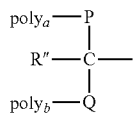

wherein:

$poly_a$ and $poly_b$ are PEG backbones (either the same or different), such as methoxy poly(ethylene glycol);

R" is a nonreactive moiety, such as H, methyl or a PEG backbone; and

P and Q are nonreactive linkages. In a preferred embodiment, the branched PEG polymer is methoxy poly(ethylene glycol) disubstituted lysine.

In addition, the PEG can comprise a forked PEG. An example of a free or nonbound forked PEG is represented by the following formula:

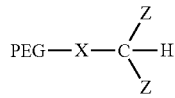

wherein: X is a spacer moiety and each Z is an activated terminal group linked to CH by a chain of atoms of defined length. The chain of atoms linking the Z functional groups to the branching carbon atom serve as a tethering group and may comprise, for example, alkyl chains, ether chains, ester chains, amide chains and combinations thereof. U.S. Pat. No. 6,362,254 discloses various forked PEG structures capable of use in the present invention.

The PEG polymer may comprise a pendant PEG molecule having reactive groups, such as carboxyl, covalently attached along the length of the PEG rather than at the end of the PEG chain. The pendant reactive groups can be attached to the PEG directly or through a spacer moiety, such as an alkylene group.

In addition to the above-described forms of PEG, each water-soluble polymer in the polymeric reagent can also be prepared with one or more weak or releasable linkages in the polymer, including any of the above described polymers. For example, PEG can be prepared with ester linkages in the polymer that are subject to hydrolysis. As shown below, this hydrolysis results in cleavage of the polymer into fragments of lower molecular weight:

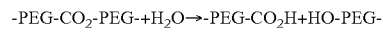

Other hydrolytically releasable linkages, useful as a releasable linkage within a polymer backbone, include carbonate linkages; imine linkages resulting, for example, from reaction of an amine and an aldehyde (see, e.g., Ouchi et al. (1997) *Polymer Preprints* 38(1):582-3); phosphate ester linkages formed, for example, by reacting an alcohol with a phosphate group; hydrazone linkages which are typically formed by reaction of a hydrazide and an aldehyde; acetal linkages that are typically formed by reaction between an aldehyde and an alcohol; ortho ester linkages that are, for example, formed by reaction between a formate and an alcohol; amide linkages formed by an amine group, e.g., at an end of a polymer such as PEG, and a carboxyl group of another PEG chain; urethane linkages formed from reaction of, e.g., a PEG with a terminal isocyanate group and a PEG alcohol; peptide linkages formed by an amine group, e.g., at an end of a polymer such as PEG, and a carboxyl group of a peptide; and oligonucleotide linkages formed by, for example, a phosphoramidite group, e.g., at the end of a polymer, and a 5' hydroxyl group of an oligonucleotide.

It is understood by those of ordinary skill in the art that the term poly(ethylene glycol) or PEG represents or includes all the above forms of PEG.

Those of ordinary skill in the art will recognize that the foregoing discussion concerning substantially water-soluble polymers is by no means exhaustive and is merely illustrative, and that all polymeric materials having the qualities described above are contemplated. As used herein, the term "water-soluble polymer" refers both to a molecule as well as the residue of water-soluble polymer that has been attached to another moiety. The following description of a water-soluble polymer are applicable not only to the polymeric reagent, but to the corresponding conjugates formed using the described polymeric reagents.

The functional group of the polymeric reagents used to form the conjugates described herein is a functional group capable of reacting with an amino group of an active agent to form a releasable linkage, such as a carbamate linkage. The invention is not limited with respect to the specific functional group so long as the functional group is capable of reacting with an amino group of an active agent to form a releasable linkage, such as a carbamate linkage. Exemplary functional groups capable of reacting with an amino group of an active agent include those functional groups selected from the group consisting of active carbonates such as N-succinimidyl, 1-benzotriazolyl, imidazole, carbonate halides (such as carbonate chloride and carbonate bromide), phenolates (such as p-nitrophenolate) and so forth. Also, as a special case, if the active agent is available with the active amine group converted into an isocyantate or isothiocyanate group, then the functional group of the polymeric reagent can be hydroxyl as the reaction of these components provide a releasable carbamate linkage.

Exemplary polymeric reagents will now be discussed in further detail. It must be remembered that while stereochemistry is not specifically shown in any formulae or structures (whether for a polymeric reagent, conjugate, or any other formula or structure), the provided formulae and structures contemplate both enantiomers, as well as compositions comprising mixtures of each enantiomer in equal amounts (i.e., a racemic mixture) and unequal amounts.

An exemplary polymeric reagent of the invention has the following structure:

$(X)_n$-(FG)

wherein:

FG is a functional group capable of reacting with an amino group of an active agent to form a releasable linkage, such as a carbamate linkage X is a radical selected from the group consisting of the group of radicals having the formulas (i) to (iv):

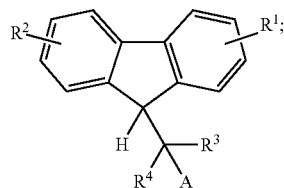

formula (i)

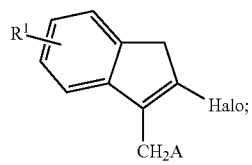

formula (ii)

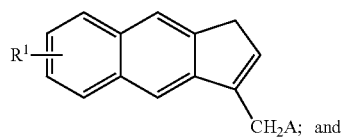

formula (iii)

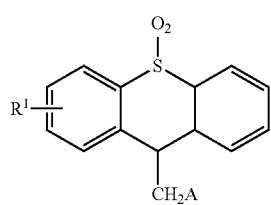

formula (iv)

wherein:

$R^1$ is a radical containing a water-soluble non peptidic polymer [such as a poly(ethylene glycol)];

$R^2$ is selected from the group consisting of hydrogen, alkyl, substituted alkyl, alkoxy, alkoxyalkyl, aryl, alkaryl, aralkyl, substituted aryl, heteroaryl, halogen, nitro, —$SO_3H$, —$SO_2NHR$, amino, ammonium, substituted ammonium, carboxyl, $PO_3H_2$, and $OPO_3H_2$;

R is selected from the group consisting of hydrogen, alkyl, aryl, and heteroaryl;

$R^3$ is selected from the group consisting of hydrogen, alkyl, aryl, and heteroaryl;

$R^4$ is selected from the group consisting of hydrogen, alkyl, aryl, and heteroaryl;

A is a covalent bond when the radical is linked to a carboxyl, phosphate or mercapto group of the drug D, or A is OCO— when the radical is linked to an amino or hydroxyl group of the drug D; and (n) is an integer of one or greater.

Exemplary polymeric reagents fall within the following formula:

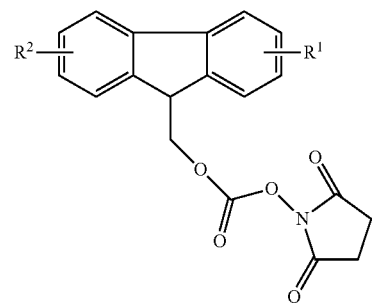

wherein:

$R^1$ is a radical of the formula: —$R^5$—$R^6$—B, $R^2$ is H or —$SO_3H$, preferably at position 2 of the fluorene ring;

B is maleimido, or —S—CO—$CH_3$ attached to a POLY $R^5$ is selected from the group consisting of —NH—, —S—, —CO—, —COO—, —$CH_2$—, —$SO_2$—, —$SO_3$—, —$PO_2$—, and —$PO_3$—; and $R^6$ is a bond or a radical by which the maleimido, —S—CO—$CH_3$ or a POLY is attached to $R^5$.

Exemplary polymeric reagents fall within the following formula:

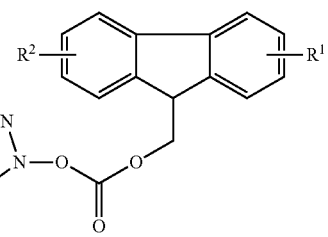

wherein:

$R^1$ is a radical of the formula: —$R^5$—$R^6$—B, $R^2$ is H or —$SO_3H$, preferably at position 2 of the fluorene ring;

B is maleimido, or —S—CO—$CH_3$ attached to a POLY $R^5$ is selected from the group consisting of —NH—, —S—, —CO—, —COO—, —$CH_2$—, —$SO_2$—, —$SO_3$—, —$PO_2$—, and —$PO_3$—; and $R^6$ is a bond or a radical by which the maleimido, —S—CO—$CH_3$ or a POLY is attached to $R^5$.

Exemplary polymeric reagents include those of the following structures:
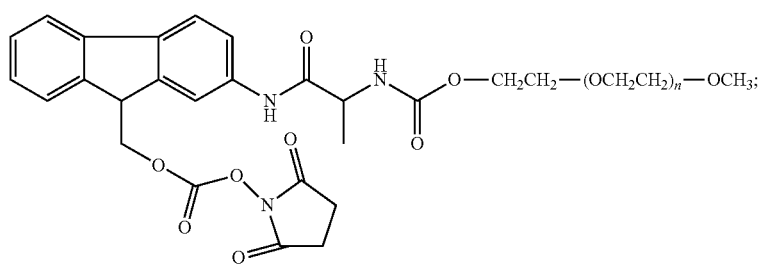
Reagent #1
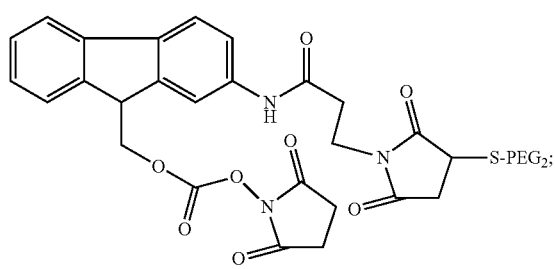
Reagent #2
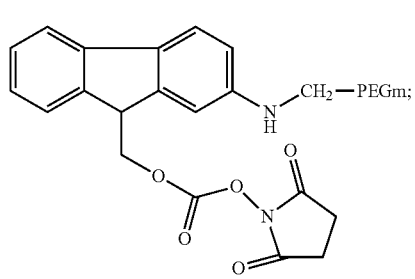
Reagent #3
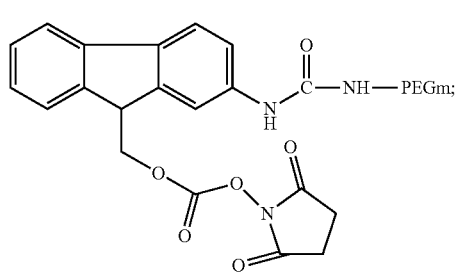
Reagent #4
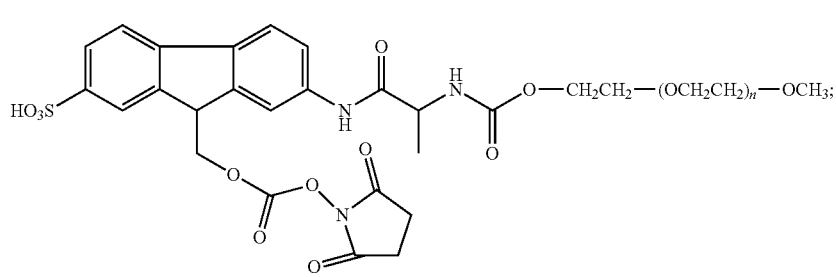
Reagent #1A Reagent #2A
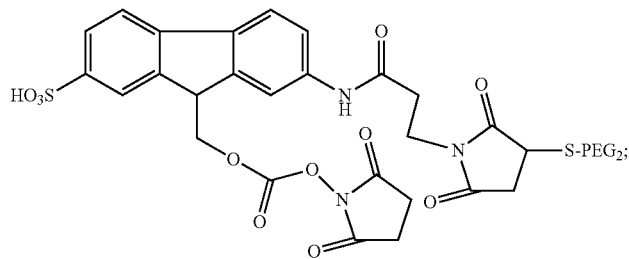
Reagent #3A
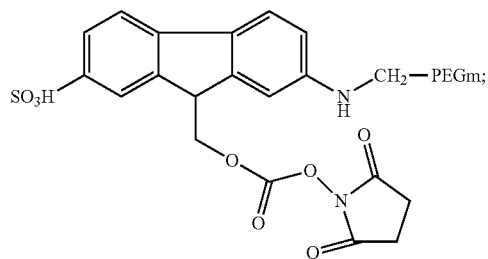
Reagent #4A
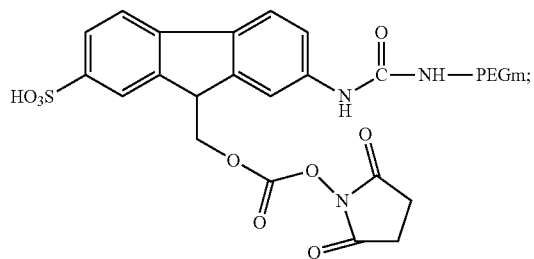
Reagent #5
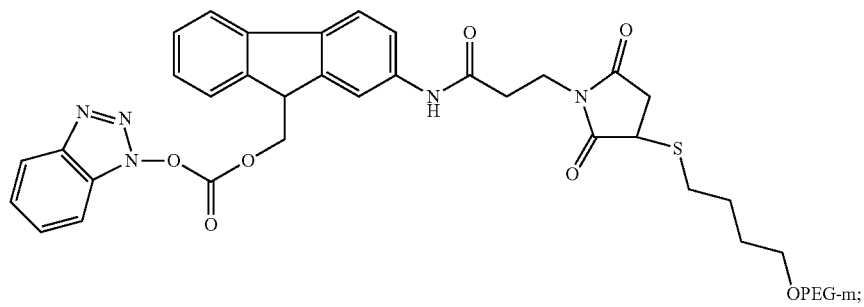
wherein PEGm is a methoxy end-capped poly(ethylene glycol) and (n) is an integer from 3 to 4000 and $PEG_2$ represents a branched PEG. POLY can be substituted for PEGm and $PEG_2$.

Further exemplary polymeric reagents include those of the following structures:
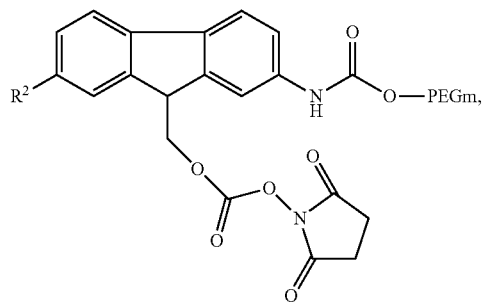
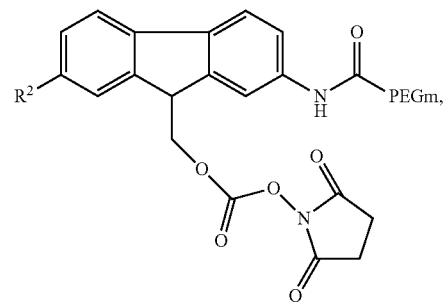
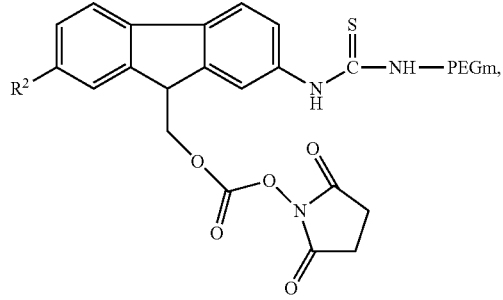
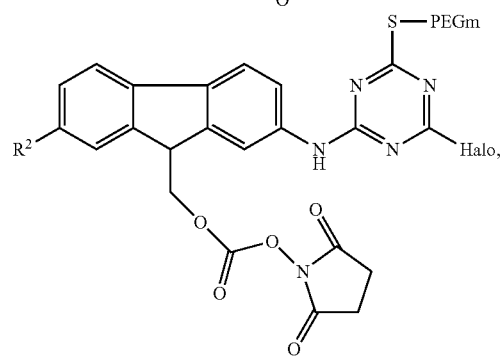
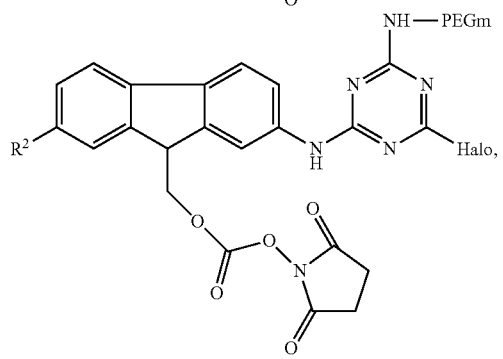
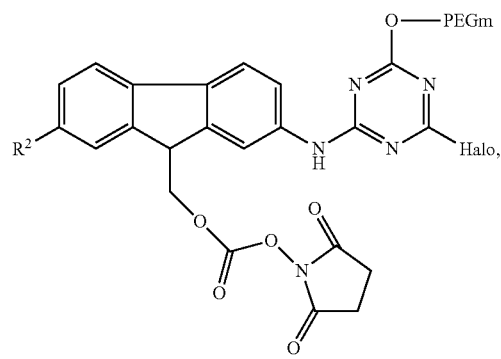
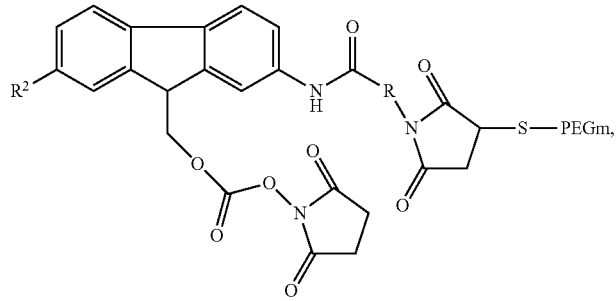
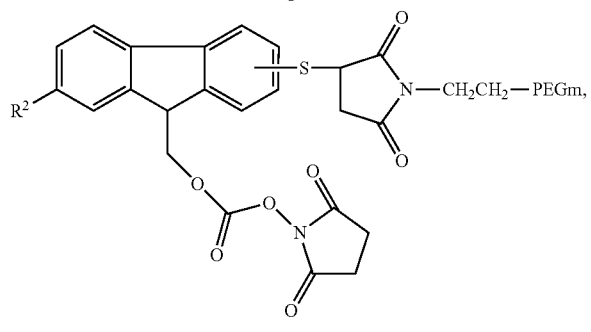
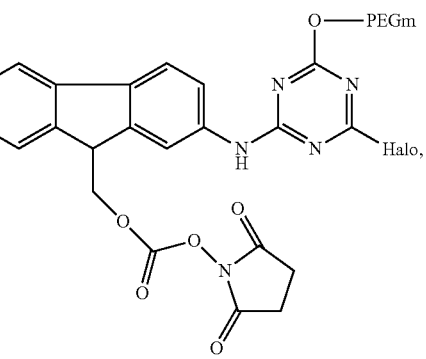

-continued
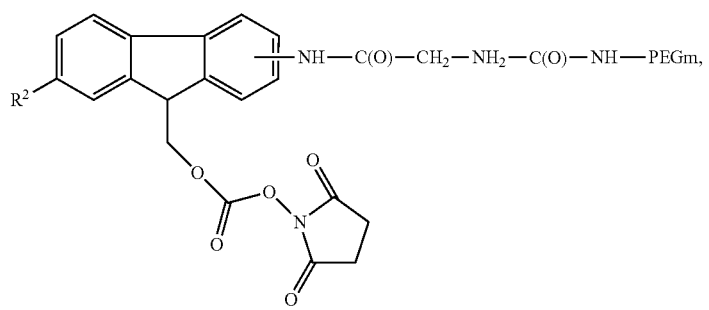
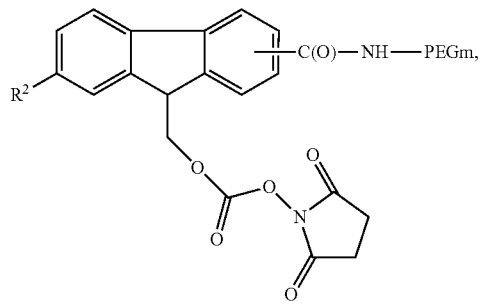
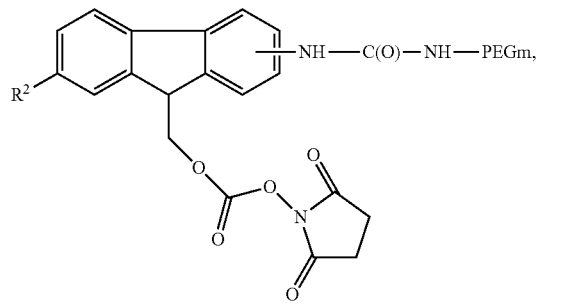
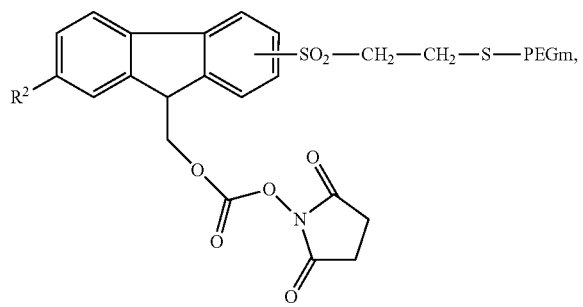
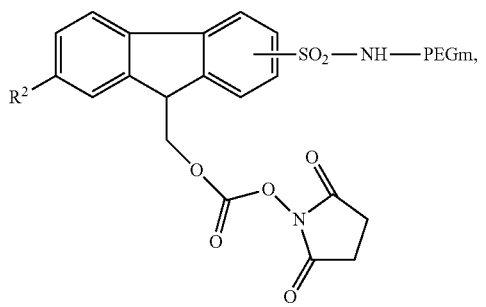
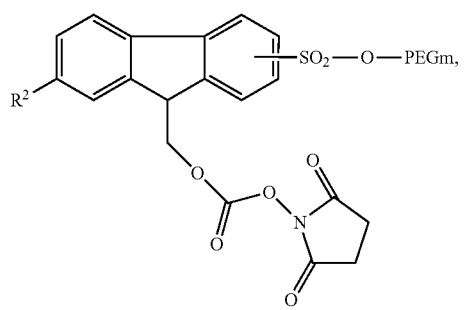
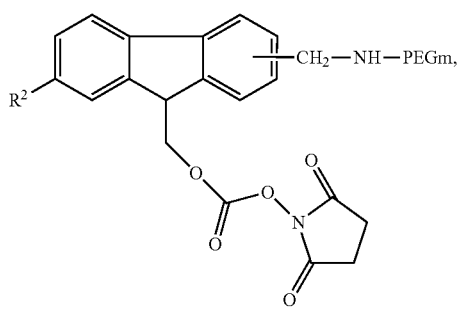
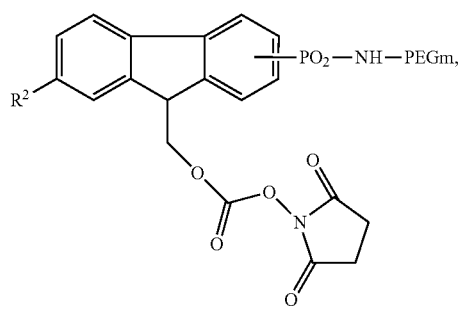
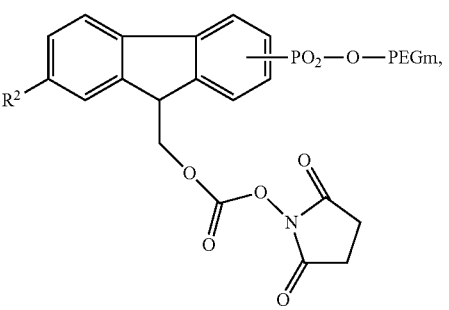

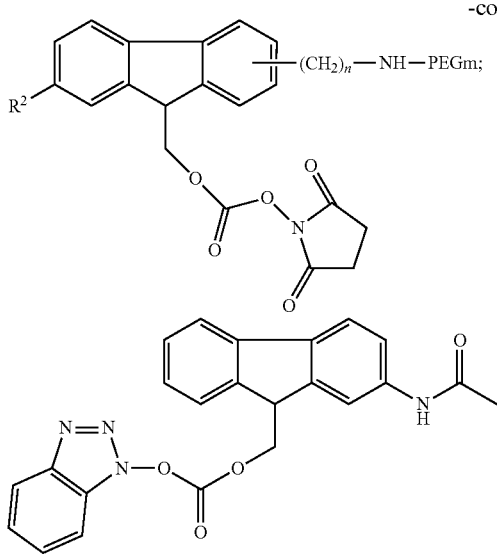
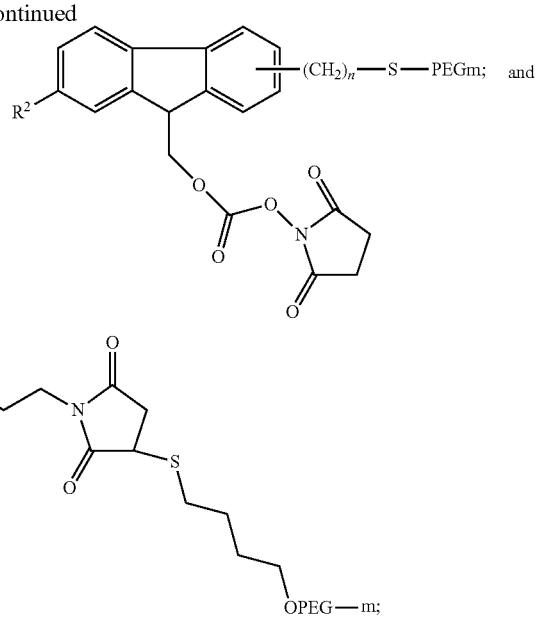

wherein PEGm is a methoxy end-capped poly(ethylene glycol), R is alkylene, Halo is selected from the group consisting of fluoro, chloro, bromo, and iodo, n' is a positive integer (e.g. 1, 2, 3, or 4), $R^2$ is H or $SO_3H$, and POLY can be substituted for PEGm.

The polymeric reagents can be prepared in any number of ways. Consequently, synthesis of the polymeric reagents is not limited to the specific technique or approach used in their preparation.

Specific approaches to prepare the polymeric reagents are described in the Experimental and in U.S. Patent Application Publication No. 2006/0160948 and WO 04/089280.

No matter which approach is used, the steps of the synthetic method take place in an appropriate solvent. One of ordinary skill in the art can determine whether any specific solvent is appropriate for any given reaction. Typically, however, the solvent is preferably a nonpolar solvent or a polar aprotic solvent. Nonlimiting examples of nonpolar solvents include benzene, xylene, dioxane, tetrahydrofuran (THF), t-butyl alcohol and toluene. Exemplary polar aprotic solvents include, but are not limited to, DMSO (dimethyl sulfoxide), HMPA (hexamethylphosphoramide), DMF (dimethylformamide), DMA (dimethylacetamide), and NMP (N-methylpyrrolidinone).

Once prepared, the polymeric reagents can be isolated. Known methods can be used to isolate the polymeric reagent, but it is particularly preferred to use chromatography, e.g., size exclusion chromatography. Alternately or in addition, the method includes the step of purifying the polymeric reagent once it is formed. Again, standard art-known purification methods can be used to purify the polymeric reagent.

The polymeric reagents are sensitive to moisture and oxygen and are ideally stored under an inert atmosphere, such as under argon or under nitrogen, and at low temperature. In this way, potentially degradative processes associated with, for example, atmospheric oxygen, are reduced or avoided entirely. In some cases, to avoid oxidative degradation, antioxidants, such as butylated hydroxyl toluene (BHT), can be added to the polymeric reagent prior to storage. In addition, it is preferred to minimize the amount of moisture associated with the storage conditions to reduce potentially damaging reactions associated with water, e.g. hydrolysis of the active ester. Moreover, it is preferred to keep the storage conditions dark in order to prevent certain degradative processes that involve light. Thus, preferred storage conditions include one or more of the following: storage under dry argon or another dry inert gas; storage at temperatures below about −15° C.; storage in the absence of light; and storage with a suitable amount (e.g., about 50 to about 500 parts per million) of an antioxidant such as BHT.

The above-described polymeric reagents are useful for conjugation to biologically active agents. For example, an amino group (e.g., primary amine) on an active agent will react with the functional group capable of reacting with an amino group of an active agent to form a releasable linkage, such as a carbamate linkage. Thus, the invention comprises a conjugate formed with any polymeric reagent described herein.

Exemplary conjugates include those of the following formula:

$$(X)_n\text{-D}$$

wherein:
D is a residue of an active agent bearing at least one functional group selected from the group consisting of amino, carboxyl, phosphate, hydroxyl, and mercapto, and
X is a radical selected from the group consisting of the group of radicals having the formulas (i) to (iv):

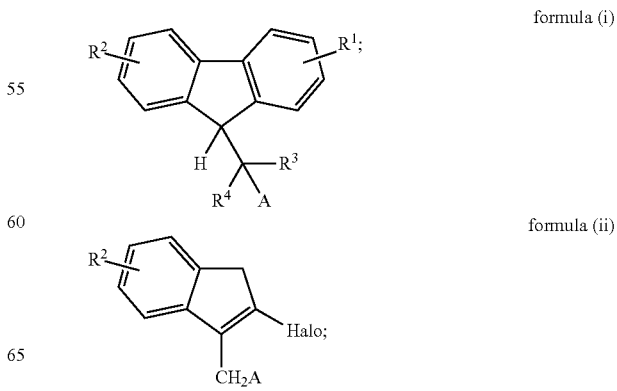

-continued formula (iii)

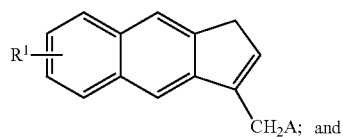

CH₂A; and formula (iv)

wherein:
R¹ is a radical containing a water-soluble polymer [such as a poly(ethylene glycol)];
R² is selected from the group consisting of hydrogen, alkyl, alkoxy, alkoxyalkyl, aryl, alkaryl, aralkyl, halogen, nitro, —SO₃H, —SO₂NHR, amino, ammonium, carboxyl, PO₃H₂, and OPO₃H₂;
R is selected from the group consisting of hydrogen, alkyl, aryl, and heteroaryl;
R³ is selected from the group consisting of hydrogen, alkyl, aryl, and heteroaryl;
R⁴ is selected from the group consisting of hydrogen, alkyl, aryl, and heteroaryl;
A is a covalent bond when the radical is linked to a carboxyl, phosphate or mercapto group of D, or A is OCO— when the radical is linked to an amino or hydroxyl group of D; and
(n) is an integer of one or greater.
Exemplary conjugates have the following structures:

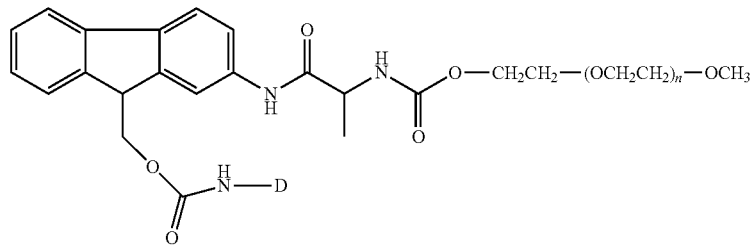

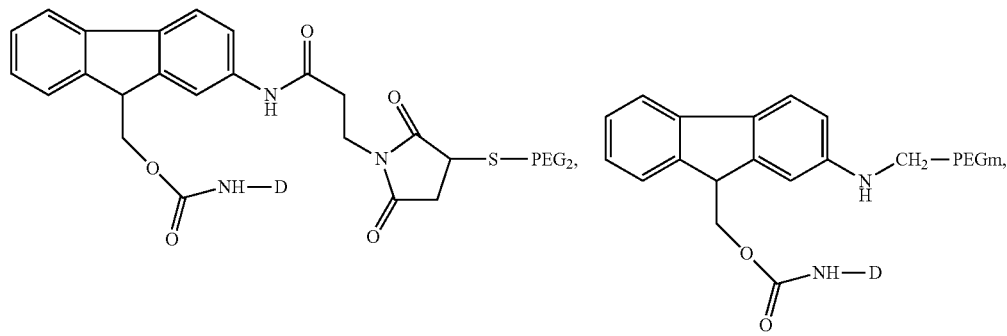

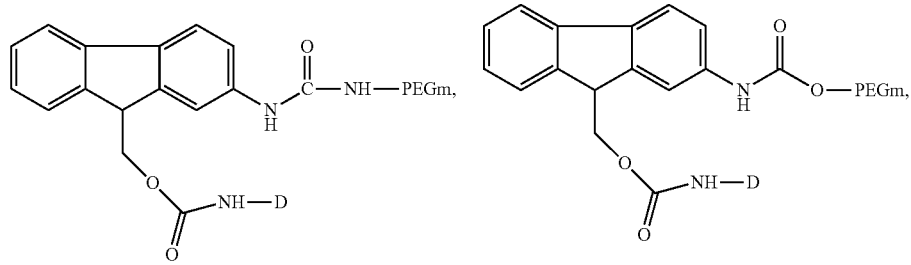

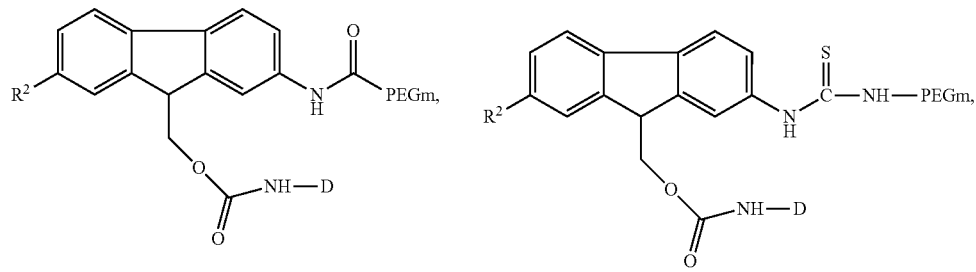

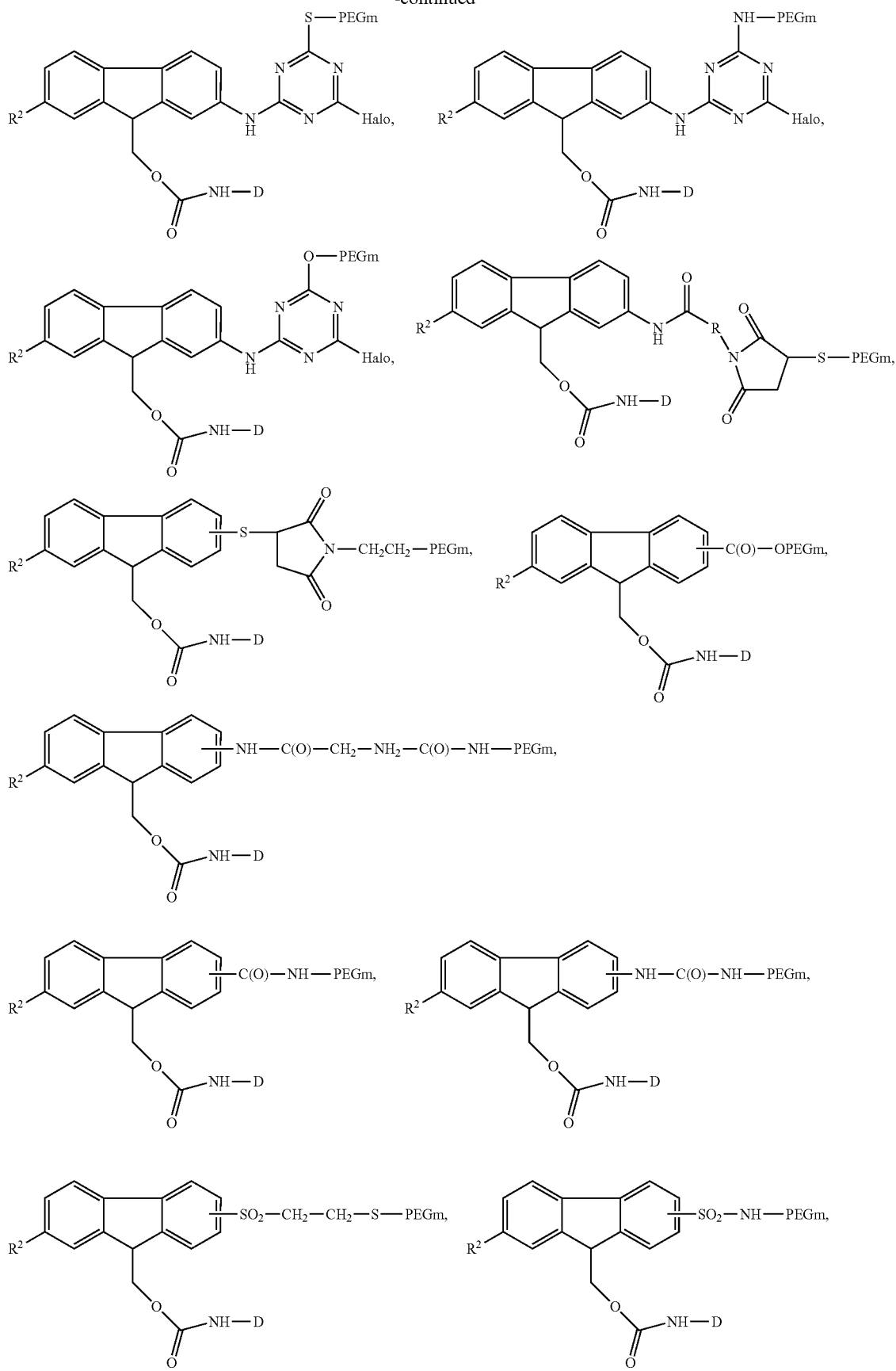

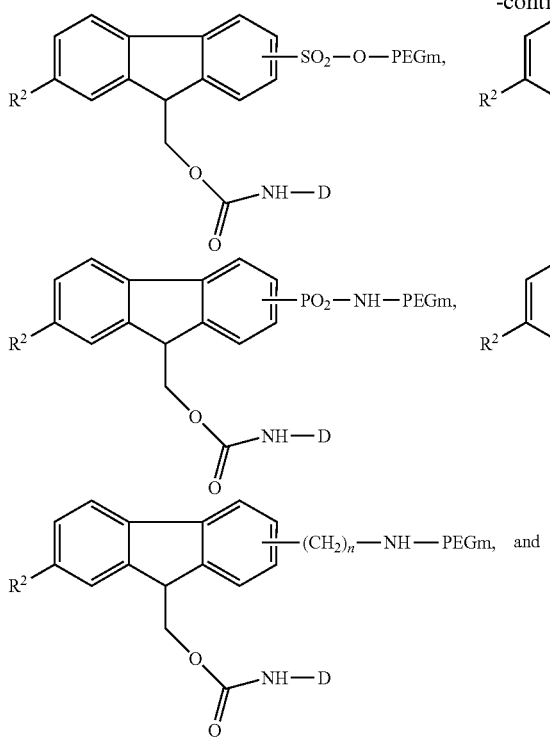
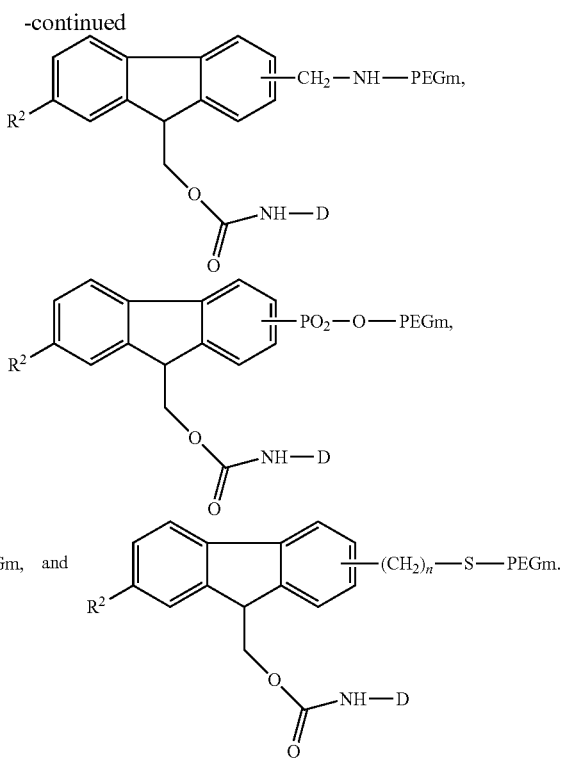

The biologically active agent, to which a polymeric reagent as described herein can be conjugated, is an amine-containing biologically active agent. In some embodiments, the biologically active agent will be a small molecule (e.g., a biologically active agent that has a molecular weight of less than about 3,500 Daltons. In other embodiments, the biologically active agent will be a macromolecule, such as a polypeptide, having a molecular weight greater than about 3,500 Daltons. Pharmacologically active polypeptides represent a preferred type of biologically active agent. It should be understood that for purposes of the present discussion, the term "polypeptide" will be generic for oligopeptides and proteins. With regard to polypeptides, the amine to which the polymeric reagent couples to can be on the N-terminus or an amine-containing side chain of an amino acid (such as lysine) within the polypeptide.

The invention also provides for a method of preparing a conjugate comprising the step of contacting a polymeric reagent with a biologically active agent under conditions suitable to form a covalent attachment between the polymer and the biologically active agent. Typically, the polymer is added to the active agent or surface at an equimolar amount (with respect to the desired number of groups suitable for reaction with the reactive group) or at a molar excess. For example, the polymeric reagent can be added to the target active agent at a molar ratio of about 1:1 (polymeric reagent: active agent), 1.5:1, 2:1, 3:1, 4:1, 5:1, 6:1, 8:1, 10:1, 20:1, 40:1, or 60:1. The conjugation reaction is allowed to proceed until substantially no further conjugation occurs, which can generally be determined by monitoring the progress of the reaction over time. Progress of the reaction can be monitored by withdrawing aliquots from the reaction mixture at various time points and analyzing the reaction mixture by SDS-PAGE or MALDI-TOF mass spectrometry or any other suitable analytical method. Once a plateau is reached with respect to the amount of conjugate formed or the amount of unconjugated polymer remaining, the reaction is assumed to be complete. Typically, the conjugation reaction takes anywhere from minutes to several hours (e.g., from 5 minutes to 24 hours or more). Mono, di-, tri- and higher orders of PEGylation will occur depending on the ratio of the protein to polymeric reagent employed and various other reaction conditions used. The resulting product mixture is preferably, but not necessarily purified, to separate out excess reagents, unconjugated reactants (e.g., active agent) undesired multi-conjugated species, and free or unreacted polymer. The resulting conjugates can then be further characterized using analytical methods such as MALDI, capillary electrophoresis, gel electrophoresis, and/or chromatography.

With respect to polymer-active agent conjugates, the conjugates can be purified to obtain/isolate different conjugated species. Alternatively, and more preferably for lower molecular weight (e.g., less than about 20 kiloDaltons, more preferably less than about 10 kiloDaltons) polymers, the product mixture can be purified to obtain the distribution of water-soluble polymer segments per active agent. For example, the product mixture can be purified to obtain an average of anywhere from one to five PEGs per active agent (e.g., polypeptide). The strategy for purification of the final conjugate reaction mixture will depend upon a number of factors, including, for example, the molecular weight of the polymer employed, the particular active agent, the desired dosing regimen, and the residual activity and in vivo properties of the individual conjugate(s).

If desired, conjugates having different molecular weights can be isolated using gel filtration chromatography. That is to say, gel filtration chromatography is used to fractionate differently numbered polymer-to-active agent ratios (e.g., 1-mer, 2-mer, 3-mer, and so forth, wherein "1-mer" indicates 1 polymer to active agent, "2-mer" indicates two polymers to active agent, and so on) on the basis of their differing molecular weights (where the difference corresponds essentially to the average molecular weight of the water-soluble polymer segments). For example, in an exemplary reaction where a 100 kDa protein is randomly conjugated to a polymeric reagent having a molecular weight of about 20 kDa, the resulting reaction mixture will likely contain unmodified protein (MW 100 kDa), mono-PEGylated protein (MW 120 kDa), di-PEGylated protein (MW 140 kDa), and so forth. While this approach can be used to separate PEG and other polymer conjugates having different molecular weights, this approach is generally ineffective for separating positional isomers having different polymer attachment sites within the protein. For example, gel filtration chromatography can be used to separate from each other mixtures of PEG 1-mers, 2-mers, 3-mers, and so forth, although each of the recovered PEG-mer compositions may contain PEGs attached to different reactive amino groups (e.g., lysine residues) within the active agent.

Gel filtration columns suitable for carrying out this type of separation include Superdex™ and Sephadex™ columns available from Amersham Biosciences (Piscataway, N.J.). Selection of a particular column will depend upon the desired fractionation range desired. Elution is generally carried out using a suitable buffer, such as phosphate, acetate, or the like. The collected fractions may be analyzed by a number of different methods, for example, (i) optical density (OD) at 280 nm for protein content, (ii) bovine serum albumin (BSA) protein analysis, (iii) iodine testing for PEG content [Sims et al. (1980) Anal. Biochem, 107:60-63], (iv) HPLC, and (v) sodium dodecyl sulfate polyacrylamide gel electrophoresis (SDS PAGE), followed by staining with barium iodide.

Separation of positional isomers is carried out by reverse phase chromatography using a reverse phase-high performance liquid chromatography (RP-HPLC) C18 column (Amersham Biosciences or Vydac) or by ion exchange chromatography using an ion exchange column, e.g., a Sepharose™ ion exchange column available from Amersham Biosciences. Either approach can be used to separate polymer-active agent isomers having the same molecular weight (positional isomers).

A biologically active agent for use in coupling to a polymer as presented herein may be any one or more of the following. Suitable agents can be selected from, for example, hypnotics and sedatives, psychic energizers, tranquilizers, respiratory drugs, anticonvulsants, muscle relaxants, antiparkinson agents (dopamine antagnonists), analgesics, anti-inflammatories, antianxiety drugs (anxiolytics), appetite suppressants, antimigraine agents, muscle contractants, anti-infectives (antibiotics, antivirals, antifungals, vaccines), antiarthritics, antimalarials, antiemetics, anepileptics, bronchodilators, cytokines, growth factors, anti-cancer agents, antithrombotic agents, antihypertensives, cardiovascular drugs, antiarrhythmics, antioxicants, anti-asthma agents, hormonal agents including contraceptives, sympathomimetics, diuretics, lipid regulating agents, antiandrogenic agents, antiparasitics, anticoagulants, neoplastics, antineoplastics, hypoglycemics, nutritional agents and supplements, growth supplements, antienteritis agents, vaccines, antibodies, diagnostic agents, and contrasting agents.

More particularly, the active agent may fall into one of a number of structural classes, including but not limited to small molecules (preferably insoluble small molecules), peptides, polypeptides, proteins, polysaccharides, steroids, nucleotides, oligonucleotides, polynucleotides, fats, electrolytes, and the like. Preferably, an active agent for coupling to a polymer as described herein possesses a native amino group, or alternatively, is modified to contain at least one reactive amino group suitable for conjugating to a polymer described herein.

Specific examples of active agents suitable for covalent attachment include but are not limited to agalsidase, alefacept, aspariginase, amdoxovir (DAPD), antide, becaplermin, calcitonins, cyanovirin, denileukin diftitox, erythropoietin (EPO), EPO agonists (e.g., peptides from about 10-40 amino acids in length and comprising a particular core sequence as described in WO 96/40749), dornase alpha, erythropoiesis stimulating protein (NESP), coagulation factors such as Factor V, Factor VII, Factor VIIa, Factor VIII, Factor IX, Factor X, Factor XI, Factor XII, Factor XIII, von Willebrand factor; ceredase, cerezyme, alpha-glucosidase, collagen, cyclosporin, alpha defensins, beta defensins, desmopressin, exedin-4, granulocyte colony stimulating factor (GCSF), thrombopoietin (TPO), alpha-1 proteinase inhibitor, elcatonin, granulocyte macrophage colony stimulating factor (GMCSF), fibrinogen, filgrastim, growth hormones human growth hormone (hGH), somatropin, growth hormone releasing hormone (GHRH), GRO-beta, GRO-beta antibody, bone morphogenic proteins such as bone morphogenic protein-2, bone morphogenic protein-6, OP-1; acidic fibroblast growth factor, basic fibroblast growth factor, CD-40 ligand, heparin, human serum albumin, low molecular weight heparin (LMWH), interferons such as interferon alpha, interferon beta, interferon gamma, interferon omega, interferon tau, consensus interferon; interleukins and interleukin receptors such as interleukin-1 receptor, interleukin-2, interluekin-2 fusion proteins, interleukin-1 receptor antagonist, interleukin-3, interleukin-4, interleukin-4 receptor, interleukin-6, interleukin-8, interleukin-12, interleukin-13 receptor, interleukin-17 receptor; lactoferrin and lactoferrin fragments, luteinizing hormone releasing hormone (LHRH), insulin, pro-insulin, insulin analogues (e.g., mono-acylated insulin as described in U.S. Pat. No. 5,922,675), amylin, C-peptide, somatostatin, somatostatin analogs including octreotide, vasopressin, follicle stimulating hormone (FSH), influenza vaccine, insulin-like growth factor (IGF), insulintropin, macrophage colony stimulating factor (M-CSF), plasminogen activators such as alteplase, urokinase, reteplase, streptokinase, pamiteplase, lanoteplase, and teneteplase; nerve growth factor (NGF), osteoprotegerin, platelet-derived growth factor, tissue growth factors, transforming growth factor-1, vascular endothelial growth factor, leukemia inhibiting factor, keratinocyte growth factor (KGF), glial growth factor (GGF), T Cell receptors, CD molecules/antigens, tumor necrosis factor (TNF), monocyte chemoattractant protein-1, endothelial growth factors, parathyroid hormone (PTH), glucagon-like peptide, somatotropin, thymosin alpha 1, rasburicase, thymosin alpha 1 IIb/IIIa inhibitor, thymosin beta 10, thymosin beta 9, thymosin beta 4, alpha-1 antitrypsin, phosphodiesterase (PDE) compounds, VLA-4 (very late antigen-4), VLA-4 inhibitors, bisphosphonates, respiratory syncytial virus antibody, cystic fibrosis transmembrane regulator (CFTR) gene, deoxyreibonuclease (Dnase), bactericidal/permeability increasing protein (BPI), and anti-CMV antibody. Exemplary monoclonal antibodies include etanercept (a dimeric fusion protein consisting of the extracellular ligand-binding portion of the human 75 kD TNF receptor linked to the Fc portion of IgG1), abciximab, adalimumab, afelimomab, alemtuzumab, antibody to B-lymphocyte, atlizumab, basiliximab, bevacizumab, biciromab, bertilimumab, CDP-571, CDP-860, CDP-870, cetuximab, clenoliximab, daclizumab, eculizumab, edrecolomab, efalizumab, epratuzumab, fontolizumab, gavilimomab, gemtuzumab ozogamicin, ibritumomab tiuxetan, infliximab, inolimomab, keliximab, labetuzumab, lerdelimumab, olizumab, radiolabeled lym-1, metelimumab, mepolizumab, mitumomab, muromonad-CD3, nebacumab, natalizumab, odulimomab, omalizumab, oregovomab, palivizumab, pemtumomab, pexelizumab, rhuMAb-VEGF, rituximab, satumomab pendetide, sevirumab, siplizumab, tositumomab, $I^{131}$tositumomab, trastuzumab, tuvirumab and visilizumab.

Additional agents suitable for covalent attachment include, but are not limited to, tacrine, memantine, rivastigmine, galantamine, donepezil, levetiracetam, repaglinide, atorvastatin, alefacept, tadalafil, vardenafil, sildenafil, fosamprenavir, oseltamivir, valacyclovir and valganciclovir, abarelix, adefovir, alfuzosin, alosetron, amifostine, amiodarone, aminocaproic acid, aminohippurate sodium, aminoglutethimide, aminolevulinic acid, aminosalicylic acid, amlodipine, amsacrine, anagrelide, anastrozole, aprepitant, aripiprazole, asparaginase, atazanavir, atomoxetine, anthracyclines, bexarotene, bicalutamide, bleomycin, bortezomib, buserelin, busulfan, cabergoline, capecitabine, carboplatin, carmustine, chlorambucin, cilastatin sodium, cisplatin, cladribine, clodronate, cyclophosphamide, cyproterone, cytarabine, camptothecins, 13-cis retinoic acid, all trans retinoic acid; dacarbazine, dactinomycin, daptomycin, daunorubicin, deferoxamine, dexamethasone, diclofenac, diethylstilbestrol, docetaxel, doxorubicin, dutasteride, eletriptan, emtricitabine, enfuvirtide, eplerenone, epirubicin, estramustine, ethinyl estradiol, etoposide, exemestane, ezetimibe, fentanyl, fexofenadine, fludarabine, fludrocortisone, fluorouracil, fluoxymesterone, flutamide, fluticazone, fondaparinux, fulvestrant, gamma-hydroxybutyrate, gefitinib, gemcitabine, epinephrine, L-Dopa, hydroxyurea, icodextrin, idarubicin, ifosfamide, imatinib, irinotecan, itraconazole, goserelin, laronidase, lansoprazole, letrozole, leucovorin, levamisole, lisinopril, lovothyroxine sodium, lomustine, mechlorethamine, medroxyprogesterone, megestrol, melphalan, memantine, mercaptopurine, mequinol, metaraminol bitartrate, methotrexate, metoclopramide, mexiletine, miglustat, mitomycin, mitotane, mitoxantrone, modafinil, naloxone, naproxen, nevirapine, nicotine, nilutamide, nitazoxanide, nitisinone, norethindrone, octreotide, oxaliplatin, palonosetron, pamidronate, pemetrexed, pergolide, pentostatin, pilcamycin, porfimer, prednisone, procarbazine, prochlorperazine, ondansetron, palonosetron, oxaliplatin, raltitrexed, rosuvastatin, sirolimus, streptozocin, pimecrolimus, sertaconazole, tacrolimus, tamoxifen, tegaserod, temozolomide, teniposide, testosterone, tetrahydrocannabinol, thalidomide, thioguanine, thiotepa, tiotropium, topiramate, topotecan, treprostinil, tretinoin, valdecoxib, celecoxib, rofecoxib, valrubicin, vinblastine, vincristine, vindesine, vinorelbine, voriconazole, dolasetron, granisetron, formoterol, fluticasone, leuprolide, midazolam, alprazolam, amphotericin B, podophylotoxins, nucleoside antivirals, aroyl hydrazones, sumatriptan, eletriptan; macrolides such as erythromycin, oleandomycin, troleandomycin, roxithromycin, clarithromycin, davercin, azithromycin, flurithromycin, dirithromycin, josamycin, spiromycin, midecamycin, loratadine, desloratadine, leucomycin, miocamycin, rokitamycin, andazithromycin, and swinolide A; fluoroquinolones such as ciprofloxacin, ofloxacin, levofloxacin, trovafloxacin, alatrofloxacin, moxifloxicin, norfloxacin, enoxacin, gatifloxacin, gemifloxacin, grepafloxacin, lomefloxacin, sparfloxacin, temafloxacin, pefloxacin, amifloxacin, fleroxacin, tosufloxacin, prulifloxacin, irloxacin, pazufloxacin, clinafloxacin, and sitafloxacin; aminoglycosides such as gentamicin, netilmicin, paramecin, tobramycin, amikacin, kanamycin, neomycin, and streptomycin, vancomycin, teicoplanin, rampolanin, mideplanin, colistin, daptomycin, gramicidin, colistimethate; polymixins such as polymixin B, capreomycin, bacitracin, penems; penicillins including penicllinase-sensitive agents like penicillin G, penicillin V; penicillinase-resistant agents like methicillin, oxacillin, cloxacillin, dicloxacillin, floxacillin, nafcillin; gram negative microorganism active agents like ampicillin, amoxicillin, and hetacillin, cillin, and galampicillin; antipseudomonal penicillins like carbenicillin, ticarcillin, azlocillin, mezlocillin, and piperacillin; cephalosporins like cefpodoxime, cefprozil, ceftbuten, ceftizoxime, ceftriaxone, cephalothin, cephapirin, cephalexin, cephradrine, cefoxitin, cefamandole, cefazolin, cephaloridine, cefaclor, cefadroxil, cephaloglycin, cefuroxime, ceforanide, cefotaxime, cefatrizine, cephacetrile, cefepime, cefixime, cefonicid, cefoperazone, cefotetan, cefmetazole, ceftazidime, loracarbef, and moxalactam, monobactams like aztreonam; and carbapenems such as imipenem, meropenem, and ertapenem, pentamidine isetionate, albuterol sulfate, lidocaine, metaproterenol sulfate, beclomethasone diprepionate, triamcinolone acetamide, budesonide acetonide, salmeterol, ipratropium bromide, flunisolide, cromolyn sodium, and ergotamine tartrate; taxanes such as paclitaxel; SN-38, and tyrphostines.

Preferred small molecules for coupling to a polymer as described herein are those having at least one naturally occurring amino group. Preferred molecules such as these include aminohippurate sodium, amphotericin B, doxorubicin, aminocaproic acid, aminolevulinic acid, aminosalicylic acid, metaraminol bitartrate, pamidronate disodium, daunorubicin, levothyroxine sodium, lisinopril, cilastatin sodium, mexiletine, cephalexin, deferoxamine, and amifostine.

Preferred peptides or proteins for coupling to a polymer as described herein include EPO, IFN-α, IFN-β, consensus IFN, Factor VIII, B-domain deleted factor VIII, Factor IX, Factor XI, Factor VII, von Willebrand Factor, GCSF, GMCSF, hGH, insulin, FSH, peptides having GLP-1 activity, desmopressin, amdoxivir, and PTH.

With respect to von Willebrand Factor ("vWF"), the von Willebrand Factor useful for the present invention includes all potential forms, including the monomeric and multimeric forms. One particularly useful form of von Willebrand Factor are homomultimers of at least two von Willebrand Factors. The von Willebrand Factor proteins may be either a biologically active derivative, or when to be used solely as a stabilizer for Factor VIII, the von Willebrand Factor may be of a form that is not biologically active. It should also be understood that the present invention encompasses different forms of von Willebrand Factor to be used in combination. For example, a composition useful for the present invention may include different multimers, different derivatives and both biologically active derivatives and derivatives not biologically active. In primary hemostatis, von Willebrand Factor serves as a bridge of platelets and specific components of the cellular matrix, such as collagen. The biological activity of von Willebrand Factor in this process can be measured in two different in vitro assays. See Turecek et al. (2002) Semin. Thromb. Hemost. 28:149-160. The ristocetin cofactor assay is based on the agglutination of fresh formalin-fixed platelets induced by the antibiotic ristocetin in the presence of von Willebrand Factor. The degree of platelet agglutination depends on the von Willebrand Factor concentration and can be measured by the turbidimetic method, e.g., by use of an aggregometer (Weiss et al. (1973) J. Clin. Invest. 52:2708-2716; Macfarlane et al. (1975) Thromb. Diath. Haemorrh. 34:306-308). The second method is the collagen binding assay, which is based on ELISA technology (Brown et Bosak (1986) Thromb. Res. 43:303-311; Favaloro (2000) Thromb. Haemost. 83:127-135). A microtiter plate is coated with type I or III collagen. Then the von Willebrand Factor is bound to the collagen surface and subsequently detected with an enzyme-labeled polyclonal antibody. The last step is the substrate reaction, which can be photometrically monitored with an ELISA reader.

von Willebrand Factor includes plasma-derived von Willebrand Factor and recombinant von Willebrand Factor. The von Willebrand Factor may be produced by any method known in the art. One specific example is disclosed in WO 86/06096.

With respect to Factors VIII, IX, or XI, the Factors VIII, IX, or XI useful for the present invention includes all potential forms, including the monomeric and multimeric forms. Also, included are the activated, or inactivated forms. It should also be understood that the present invention encompasses different forms of Factors VIII, IX, or XI to be used in combination. For example, a composition useful for the present invention may include different multimers, different derivatives and both biologically active derivatives and derivatives not biologically active. The biologically activity of Factors VIII, IX, or XI in this process can be measured in many different in vitro assays (Turecek et al. (2002) Semin. Thromb. Hemost. 28:149-160. The degree of platelet agglutination (or clotting time), depends on concentrations of many clotting factors and can be measured by the turbidimetic method, e.g., by use of an aggregometer (Weiss et al. (1973) J. Clin. Invest. 52:2708-2716; Macfarlane et al. (1975) Thromb. Diath. Haemorrh. 34:306-308. Another approach is a thrombin generation assay (TGA) that measures the whole kinetics of thrombin generation even after the clot formation, and thus assesses all activating and inactivating systems of coagulation (Varadi et al. (2004) Haemophilia. 10 Suppl 2:17-21.

Factor VIII, IX, or XI includes plasma-derived Factors and recombinantly synthesized factors. The Factor VIII, IX, or XI may be produced by methods known in the art.

In certain instances it is preferred that the active agent is an agent that is not insulin, an interferon, a PYY agonist, an exendin-3, an exendin-4, atrial natriuretic peptide, hGH, erythropoietin, TNF-α, calcitonin, gonadotropin releasing hormone, leuprolide, D-Lys$^6$-GnRH, hirudin, glucagon, monoclonal antibody fragments, and derivatives and analogs of each of the foregoing.

The above exemplary biologically active agents for use herein are meant to encompass, where applicable, analogues, agonists, antagonists, inhibitors, isomers, and pharmaceutically acceptable salt forms thereof. In reference to peptides and proteins, the invention is intended to encompass synthetic, recombinant, native, glycosylated, and non-glycosylated forms, as well as biologically active fragments thereof. In addition, the term "active agent" is intended to encompass the active agent prior to conjugation as well as the active agent "residue" following conjugation.

The present invention also includes pharmaceutical preparations comprising a conjugate as provided herein in combination with a pharmaceutical excipient. Generally, the conjugate itself will be in a solid form (e.g., a precipitate), which can be combined with a suitable pharmaceutical excipient that can be in either solid or liquid form.

Exemplary excipients include, without limitation, those selected from the group consisting of carbohydrates, inorganic salts, antimicrobial agents, antioxidants, surfactants, buffers, acids, bases, and combinations thereof.

A carbohydrate such as a sugar, a derivatized sugar such as an alditol, aldonic acid, an esterified sugar, and/or a sugar polymer may be present as an excipient. Specific carbohydrate excipients include, for example: monosaccharides, such as fructose, maltose, galactose, glucose, D-mannose, sorbose, and the like; disaccharides, such as lactose, sucrose, trehalose, cellobiose, and the like; polysaccharides, such as raffinose, melezitose, maltodextrins, dextrans, starches, and the like; and alditols, such as mannitol, xylitol, maltitol, lactitol, xylitol, sorbitol (glucitol), pyranosyl sorbitol, myoinositol, and the like.

The excipient can also include an inorganic salt or buffer such as citric acid, sodium chloride, potassium chloride, sodium sulfate, potassium nitrate, sodium phosphate monobasic, sodium phosphate dibasic, and combinations thereof.

The preparation may also include an antimicrobial agent for preventing or deterring microbial growth. Nonlimiting examples of antimicrobial agents suitable for the present invention include benzalkonium chloride, benzethonium chloride, benzyl alcohol, cetylpyridinium chloride, chlorobutanol, phenol, phenylethyl alcohol, phenylmercuric nitrate, thimersol, and combinations thereof.

An antioxidant can be present in the preparation as well. Antioxidants are used to prevent oxidation, thereby preventing the deterioration of the conjugate or other components of the preparation. Suitable antioxidants for use in the present invention include, for example, ascorbyl palmitate, butylated hydroxyanisole, butylated hydroxytoluene, hypophosphorous acid, monothioglycerol, propyl gallate, sodium bisulfite, sodium formaldehyde sulfoxylate, sodium metabisulfite, and combinations thereof.

A surfactant may be present as an excipient. Exemplary surfactants include: polysorbates, such as "Tween 20" and "Tween 80," and pluronics such as F68 and F88 (both of which are available from BASF, Mount Olive, N.J.); sorbitan esters; lipids, such as phospholipids such as lecithin and other phosphatidylcholines, phosphatidylethanolamines (although preferably not in liposomal form), fatty acids and fatty esters; steroids, such as cholesterol; and chelating agents, such as EDTA, zinc and other such suitable cations.

Acids or bases may be present as an excipient in the preparation. Nonlimiting examples of acids that can be used include those acids selected from the group consisting of hydrochloric acid, acetic acid, phosphoric acid, citric acid, malic acid, lactic acid, formic acid, trichloroacetic acid, nitric acid, perchloric acid, phosphoric acid, sulfuric acid, fumaric acid, and combinations thereof. Examples of suitable bases include, without limitation, bases selected from the group consisting of sodium hydroxide, sodium acetate, ammonium hydroxide, potassium hydroxide, ammonium acetate, potassium acetate, sodium phosphate, potassium phosphate, sodium citrate, sodium formate, sodium sulfate, potassium sulfate, potassium fumerate, and combinations thereof.

The pharmaceutical preparations encompass all types of formulations and in particular those that are suited for injection, e.g., powders that can be reconstituted as well as suspensions and solutions. The amount of the conjugate (i.e., the conjugate formed between the active agent and the polymer described herein) in the composition will vary depending on a number of factors, but will optimally be a therapeutically effective dose when the composition is stored in a unit dose container (e.g., a vial). In addition, the pharmaceutical preparation can be housed in a syringe. A therapeutically effective dose can be determined experimentally by repeated administration of increasing amounts of the conjugate in order to determine which amount produces a clinically desired endpoint.

The amount of any individual excipient in the composition will vary depending on the activity of the excipient and particular needs of the composition. Typically, the optimal amount of any individual excipient is determined through routine experimentation, i.e., by preparing compositions containing varying amounts of the excipient (ranging from low to high), examining the stability and other parameters, and then determining the range at which optimal performance is attained with no significant adverse effects.

Generally, however, the excipient will be present in the composition in an amount of about 1% to about 99% by weight, preferably from about 5%-98% by weight, more preferably from about 15-95% by weight of the excipient, with concentrations less than 30% by weight most preferred.

These foregoing pharmaceutical excipients along with other excipients are described in "Remington: The Science & Practice of Pharmacy", 19$^{th}$ ed., Williams & Williams, (1995), the "Physician's Desk Reference", 52$^{nd}$ ed., Medical Economics, Montvale, N.J. (1998), and Kibbe, A. H., Handbook of Pharmaceutical Excipients, 3$^{rd}$ Edition, American Pharmaceutical Association, Washington, D.C., 2000.

The pharmaceutical preparations of the present invention are typically, although not necessarily, administered via injection and are therefore generally liquid solutions or suspensions immediately prior to administration. The pharmaceutical preparation can also take other forms such as syrups, creams, ointments, tablets, powders, and the like. Other modes of administration are also included, such as pulmonary, rectal, transdermal, transmucosal, oral, intrathecal, subcutaneous, intra-arterial, and so forth.

As previously described, the conjugates can be administered parenterally by intravenous injection, or less preferably by intramuscular or by subcutaneous injection. Suitable formulation types for parenteral administration include ready-for-injection solutions, dry powders for combination with a solvent prior to use, suspensions ready for injection, dry insoluble compositions for combination with a vehicle prior to use, and emulsions and liquid concentrates for dilution prior to administration, among others.

In some embodiments of the invention, the compositions comprising the peptide-polymer conjugates may further be incorporated into a suitable delivery vehicle. Such delivery vehicles may provide controlled and/or continuous release of the conjugates and may also serve as a targeting moiety. Non-limiting examples of delivery vehicles include, adjuvants, synthetic adjuvants, microcapsules, microparticles, liposomes, and yeast cell wall particles. Yeast cells walls may be variously processed to selectively remove protein component, glucan, or mannan layers, and are referred to as whole glucan particles (WGP), yeast beta-glucan mannan particles (YGMP), yeast glucan particles (YGP), \Rhodotorula yeast cell particles (YCP). Yeast cells such as *S. cerevisiae* and *Rhodotorula* sp. are preferred; however, any yeast cell may be used. These yeast cells exhibit different properties in terms of hydrodynamic volume and also differ in the target organ where they may release their contents. The methods of manufacture and characterization of these particles are described in U.S. Pat. Nos. 5,741,495; 4,810,646; 4,992,540; 5,028,703; 5,607,677, and US Patent Applications Nos. 2005/0281781, and 2008/0044438.

The invention also provides a method for administering a conjugate as provided herein to a patient suffering from a condition that is responsive to treatment with the conjugate. The method comprises administering, generally via injection, a therapeutically effective amount of the conjugate (preferably provided as part of a pharmaceutical preparation). The method of administering may be used to treat any condition that can be remedied or prevented by administration of the particular conjugate. Those of ordinary skill in the art appreciate which conditions a specific conjugate can effectively treat. The actual dose to be administered will vary depending upon the age, weight, and general condition of the subject as well as the severity of the condition being treated, the judgment of the health care professional, and conjugate being administered. Therapeutically effective amounts are known to those skilled in the art and/or are described in the pertinent reference texts and literature. Generally, a therapeutically effective amount will range from about 0.001 mg to 100 mg, preferably in doses from 0.01 mg/day to 75 mg/day, and more preferably in doses from 0.10 mg/day to 50 mg/day.

The unit dosage of any given conjugate (again, preferably provided as part of a pharmaceutical preparation) can be administered in a variety of dosing schedules depending on the judgment of the clinician, needs of the patient, and so forth. The specific dosing schedule will be known by those of ordinary skill in the art or can be determined experimentally using routine methods. Exemplary dosing schedules include, without limitation, administration five times a day, four times a day, three times a day, twice daily, once daily, three times weekly, twice weekly, once weekly, twice monthly, once monthly, and any combination thereof. Once the desired clinical endpoint has been achieved, dosing of the composition is halted.

\It is to be understood that while the invention has been described in conjunction with the preferred specific embodiments thereof, that the foregoing description as well as the experimental that follow are intended to illustrate and not limit the scope of the invention. Other aspects, advantages and modifications within the scope of the invention will be apparent to those skilled in the art to which the invention pertains.

All articles, books, patents, patent publications and other publications referenced herein are hereby incorporated by reference in their entireties.

EXPERIMENTAL

The practice of the invention will employ, unless otherwise indicated, conventional techniques of organic synthesis and the like, which are understood by one of ordinary skill in the art and are explained in the literature. In the following examples, efforts have been made to ensure accuracy with respect to numbers used (e.g., amounts, temperatures, and so forth), but some experimental error and deviation should be accounted for. Unless otherwise indicated, temperature is in degrees Celsius and pressure is at or near atmospheric pressure at sea level. All reagents were obtained commercially unless otherwise indicated. All processing is carried out in glass or glass-lined vessels and contact with metal-containing vessels or equipment is avoided.

MATERIALS: All precursor reagents referred to in these examples are commercially available unless otherwise indicated.

Example 1

Preparation of Reagent #1 and Reagent #1A

Reagent #1 and Reagent #1A are prepared in accordance with the following synthetic approach shown schematically below.

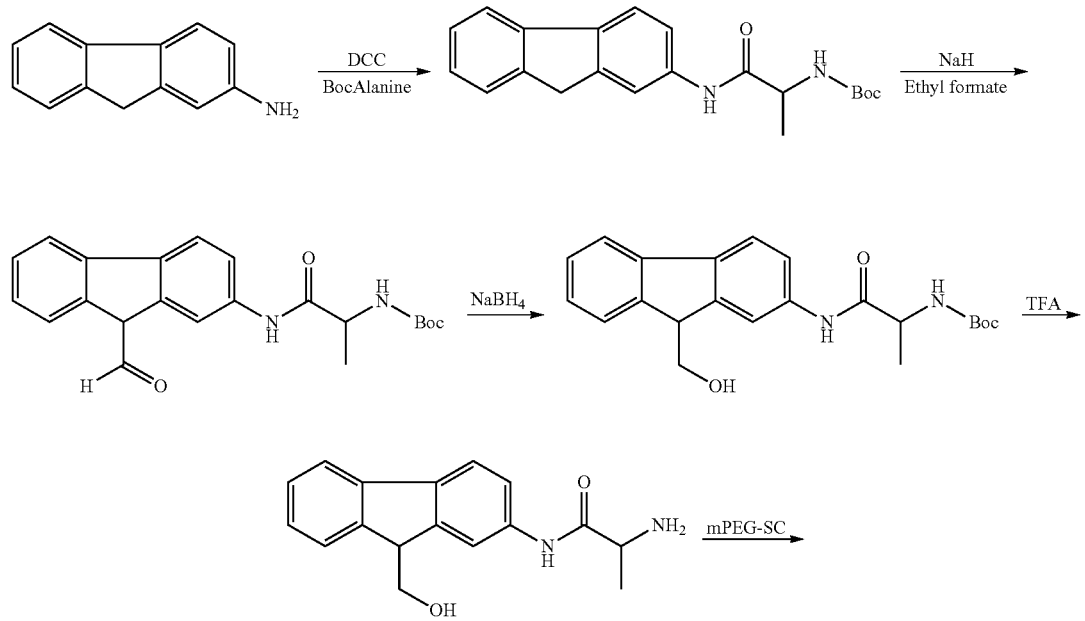

-continued

[Reagent #1 structure with fluorene, alanine, PEG, and NHS carbonate groups]

Reagent #1 optionally, ClSO₃H ↓

[Reagent #1A structure — sulfonated fluorene version]

Reagent #1A

Example 2

Preparation of von Willebrand Factor Conjugate #1 von Willebrand Factor Conjugate #1 is prepared in accordance with the following synthetic approach shown schematically below.

[Reagent #1 structure] —vWF-NH₂→

Reagent #1

[vWF Conjugate #1 structure showing carbamate linkage to vWF]

vWF Conjugate #1

Example 3
Preparation of Factor VIII Conjugate #1
Factor VIII Conjugate #1 is prepared in accordance with the following synthetic approach shown schematically below.
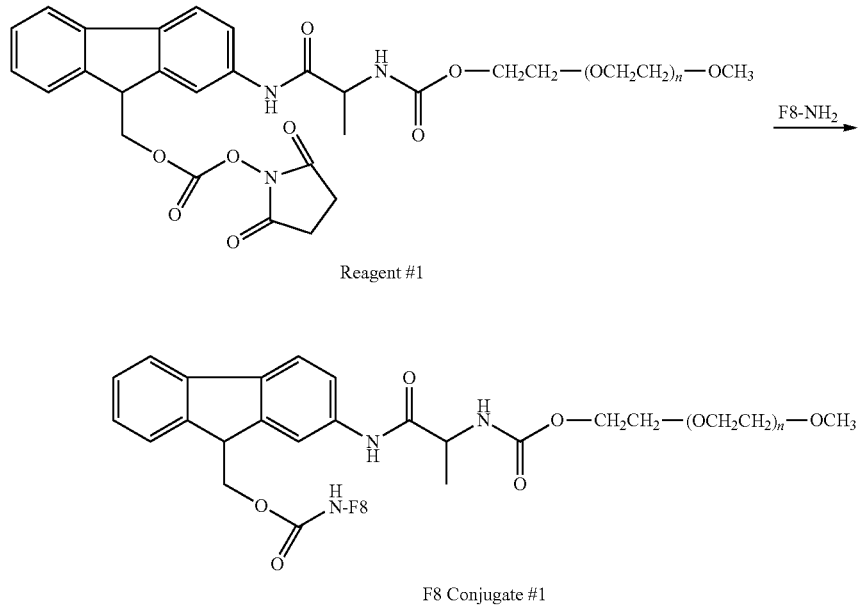
Example 4
Preparation of Factor IX Conjugate #1
Factor IX (FIX) Conjugate #1 is prepared in accordance with the following synthetic approach shown schematically below.
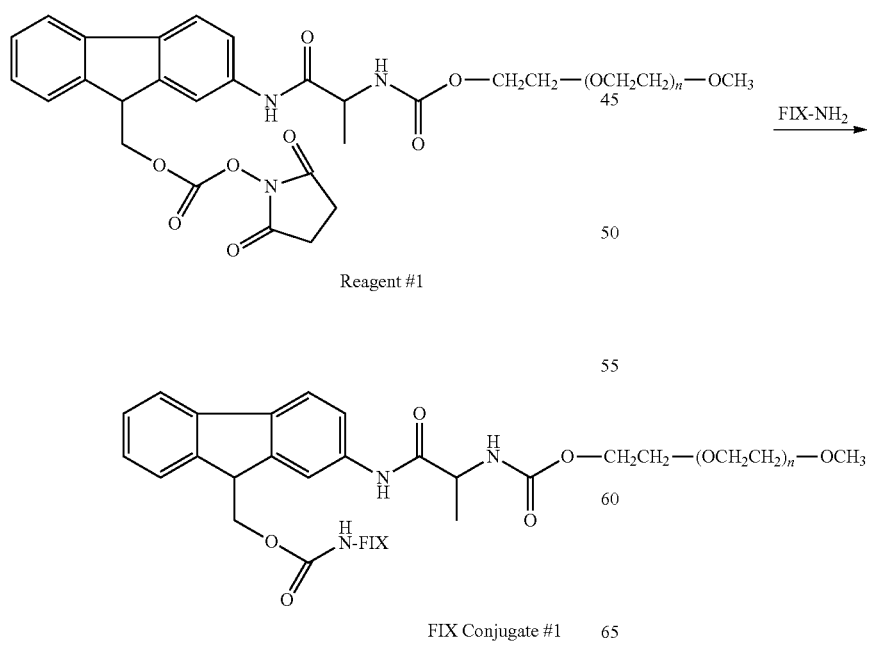

Example 5

Preparation of Factor XI Conjugate #1

Factor XI (FXI) Conjugate #1 is prepared in accordance with the following synthetic approach shown schematically below.

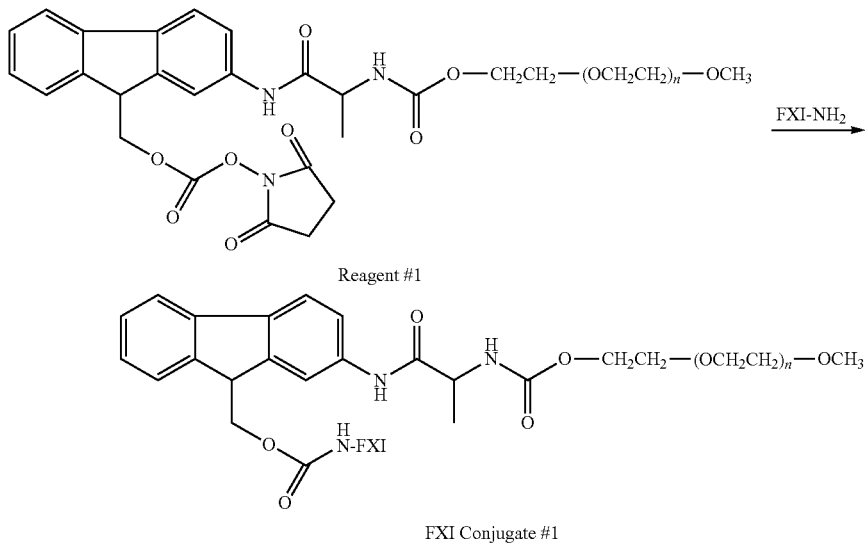

Conjugates of Factor VIII, von Willebrand Factor, Factor IX, and Factor XI are similarly prepared using Reagent #1A.

Example 6

Preparation of Reagent #2 and Reagent #2A

Reagent #2 and Reagent #2A are prepared in accordance with the following synthetic approach shown schematically below.

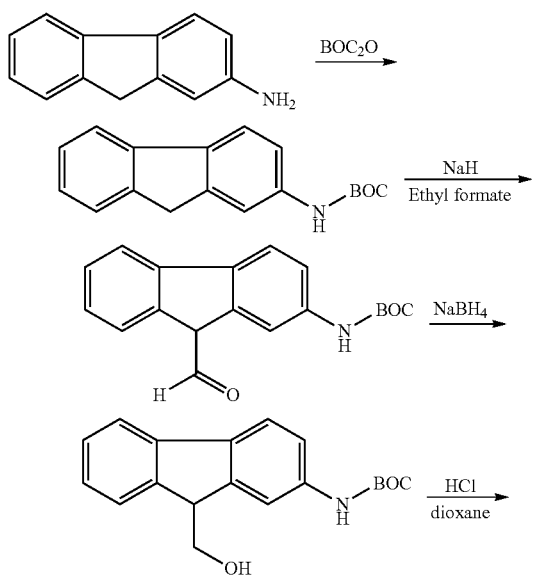

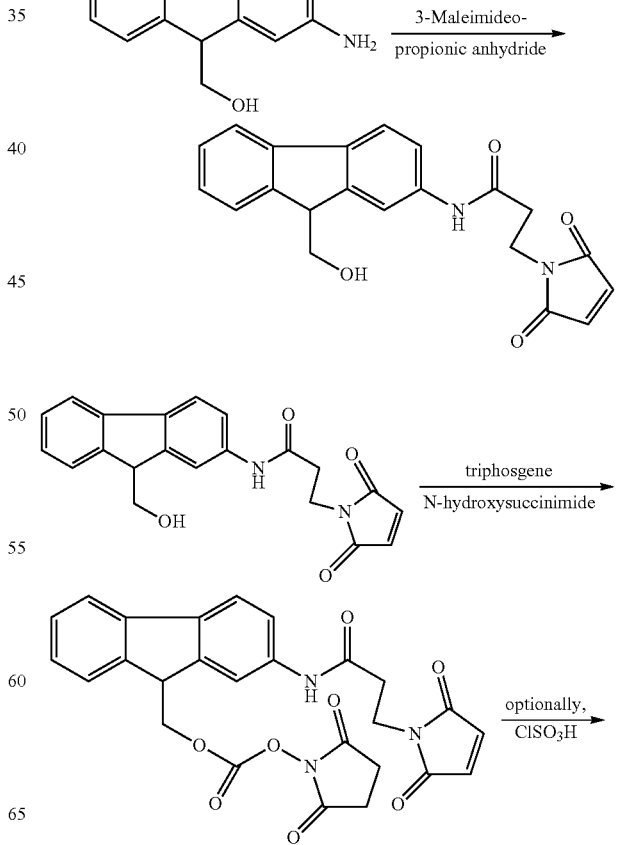

-continued

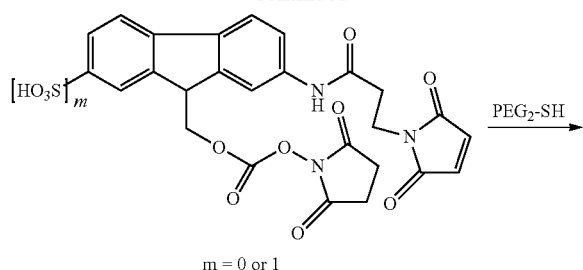

m = 0 or 1

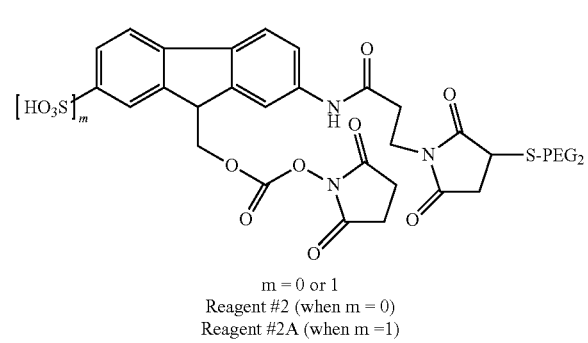

m = 0 or 1
Reagent #2 (when m = 0)
Reagent #2A (when m = 1)

Example 7

Preparation of von Willebrand Factor Conjugate #2 von Willebrand Factor Conjugate #2 is prepared in accordance with the following synthetic approach shown schematically below.

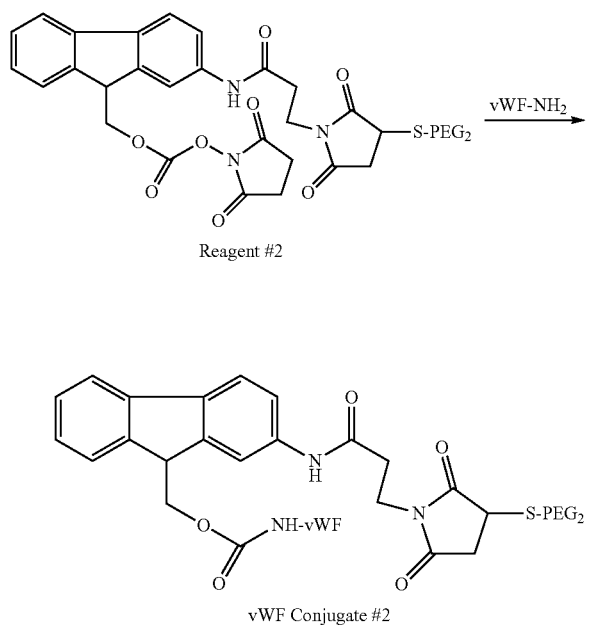

Reagent #2 vWF Conjugate #2

Example 8

Preparation of Factor VIII Conjugate #2

Factor VIII Conjugate #2 is prepared in accordance with the following synthetic approach shown schematically below.

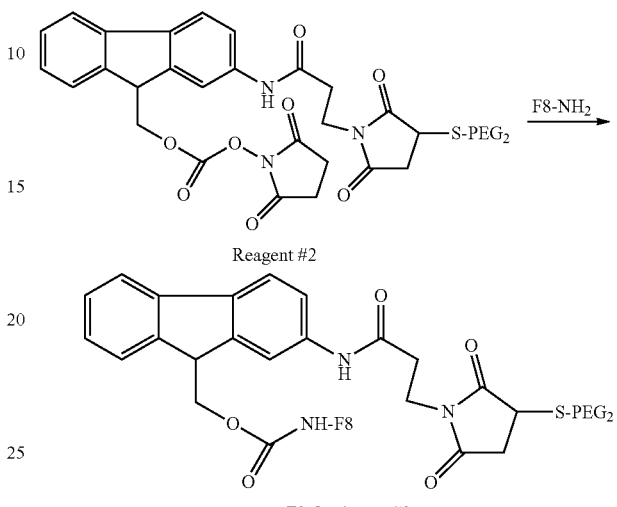

Reagent #2

F8 Conjugate #2

Example 9

Preparation of Factor IX Conjugate #2

Factor IX (FIX) Conjugate #2 is prepared in accordance with the following synthetic approach shown schematically below.

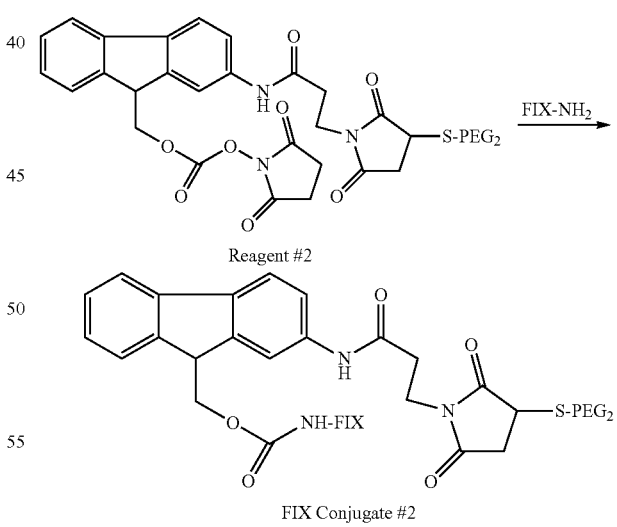

Reagent #2

FIX Conjugate #2

Example 10

Preparation of Factor XI Conjugate #2

Factor XI (FXI) Conjugate #2 is prepared in accordance with the following synthetic approach shown schematically below.

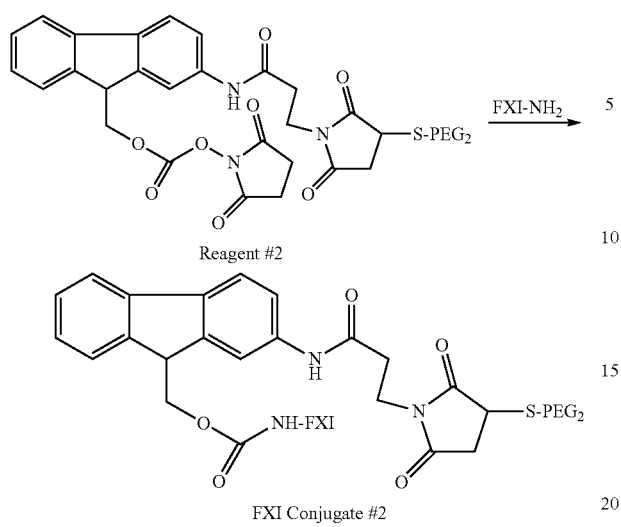

Reagent #2

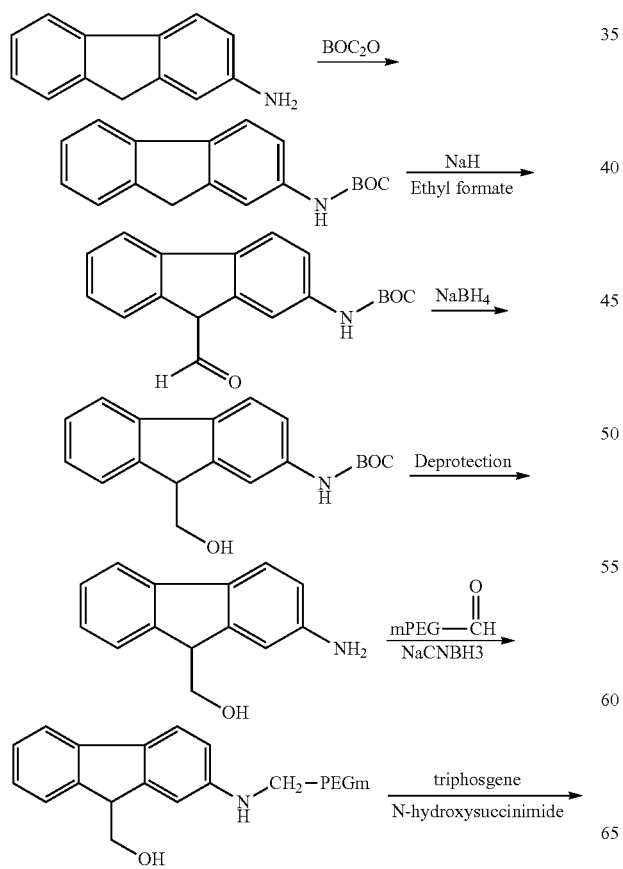

FXI Conjugate #2

Conjugates of Factor VIII, von Willebrand Factor, Factor IX, and Factor XI are similarly prepared using Reagent #2A.

Example 11

Preparation of Reagent #3 and Reagent #3A

Reagent #3 and Reagent #3A are prepared in accordance with the following synthetic approach shown schematically below.

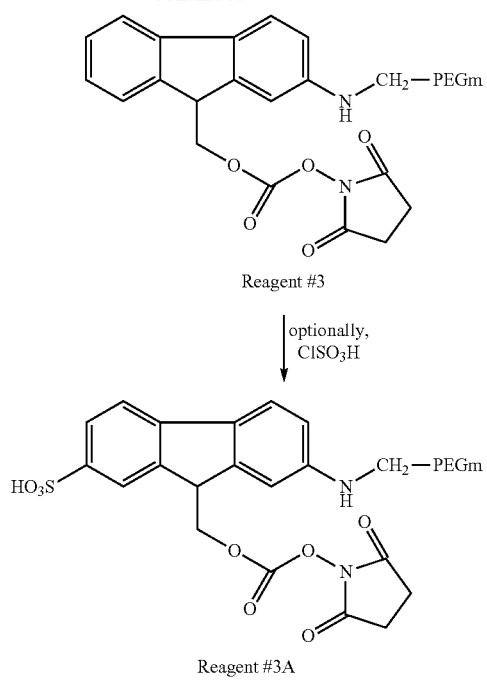

Reagent #3

Reagent #3A

Example 12

Preparation of von Willebrand Factor Conjugate #3 von Willebrand Factor Conjugate #3 is prepared in accordance with the following synthetic approach shown schematically below.

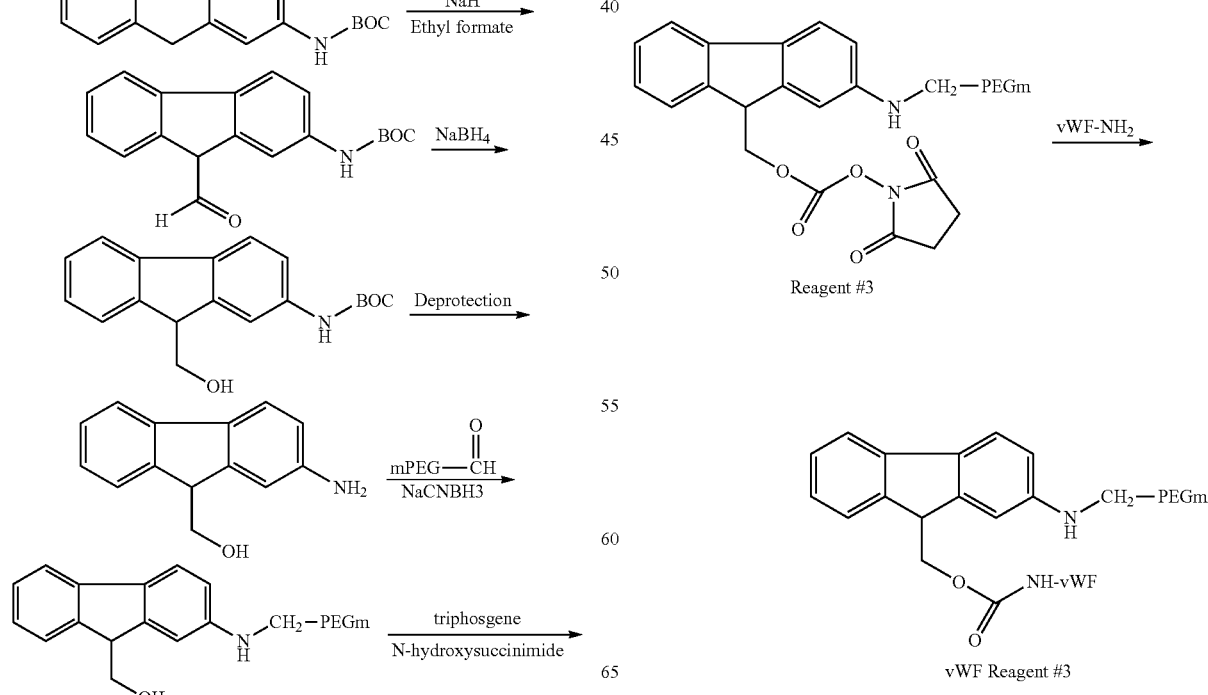

Reagent #3 vWF Reagent #3

Example 13

Preparation of Factor VIII Conjugate #3

Factor VIII Conjugate #3 is prepared in accordance with the following synthetic approach shown schematically below.

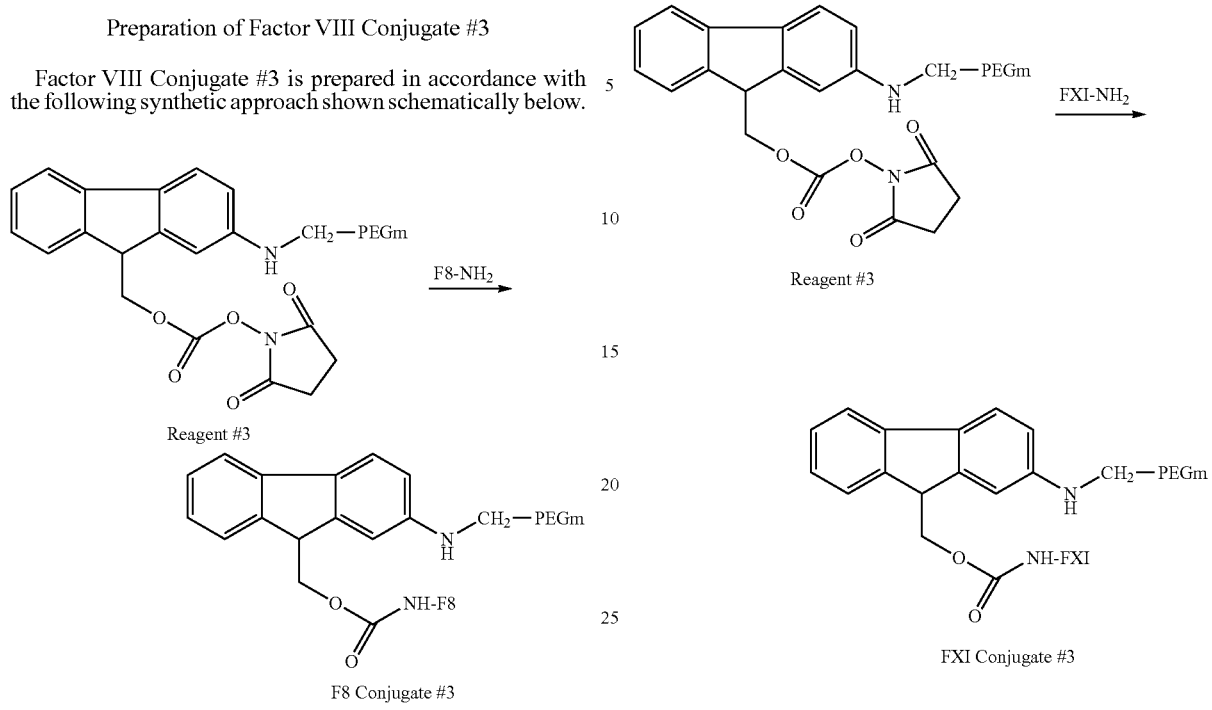

Example 14

Preparation of Factor IX Conjugate #3

Factor IX (FIX) Conjugate #3 is prepared in accordance with the following synthetic approach shown schematically below.

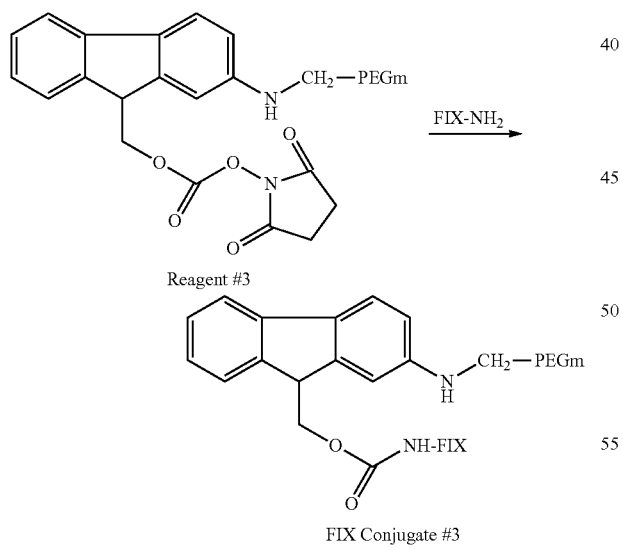

Example 15

Preparation of Factor XI Conjugate #3

Factor XI (FXI) Conjugate #3 is prepared in accordance with the following synthetic approach shown schematically below.

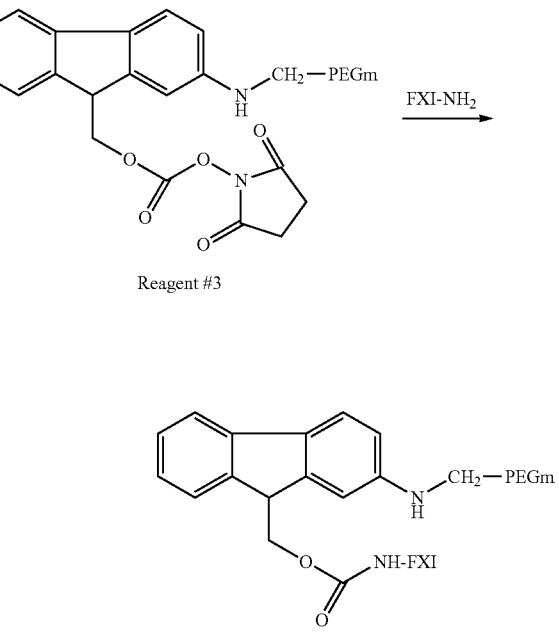

Example 16

Preparation of von Willebrand Factor Conjugate #3A von Willebrand Factor Conjugate #3A is prepared in accordance with the following synthetic approach shown schematically below.

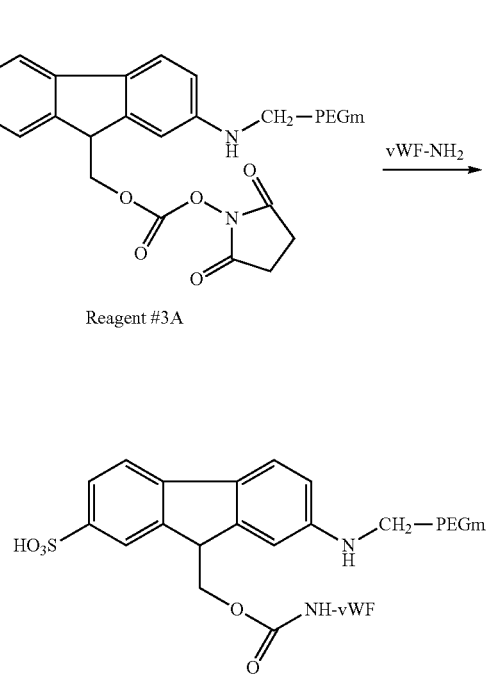

Example 17

Preparation of Factor VIII Conjugate #3A

Factor VIII Conjugate #3A is prepared in accordance with the following synthetic approach shown schematically below.

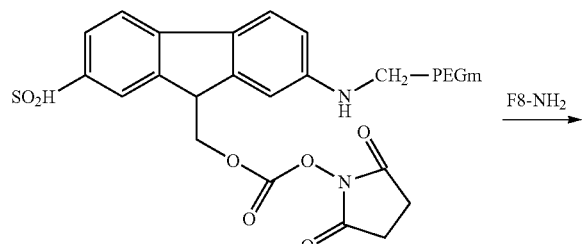

Reagent #3A

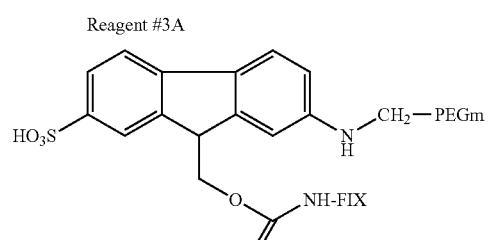

F8 Conjugate #3A

Example 18

Preparation of Factor IX Conjugate #3A

Factor IX (FIX) Conjugate #3A is prepared in accordance with the following synthetic approach shown schematically below.

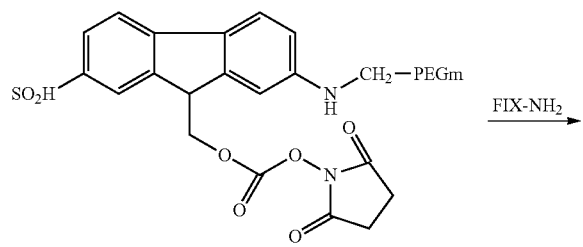

Reagent #3A

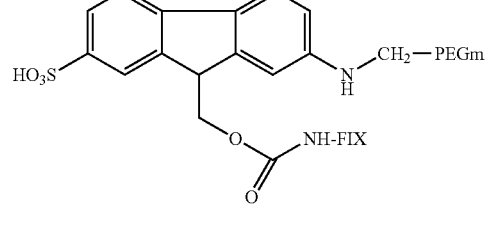

FIX Conjugate #3A

Example 19

Preparation of Factor XI Conjugate #3A

Factor XI (FXI) Conjugate #3A is prepared in accordance with the following synthetic approach shown schematically below.

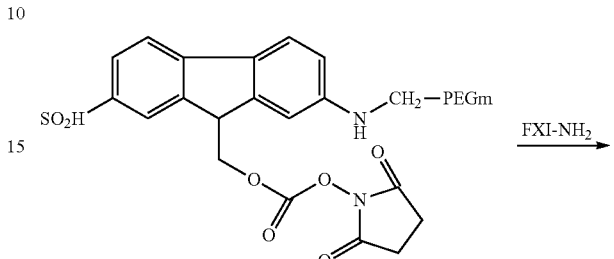

Reagent #3A

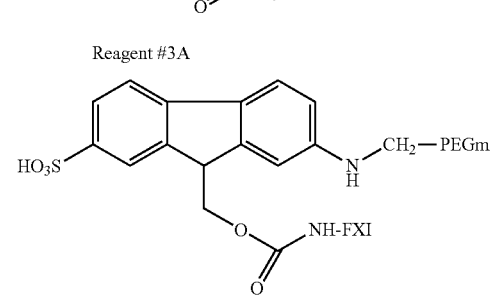

FXI Conjugate #3A

Example 20

Preparation of Reagent #4 and Reagent #4A

Reagent #4 and Reagent #4A are prepared in accordance with the following synthetic approach shown schematically below.

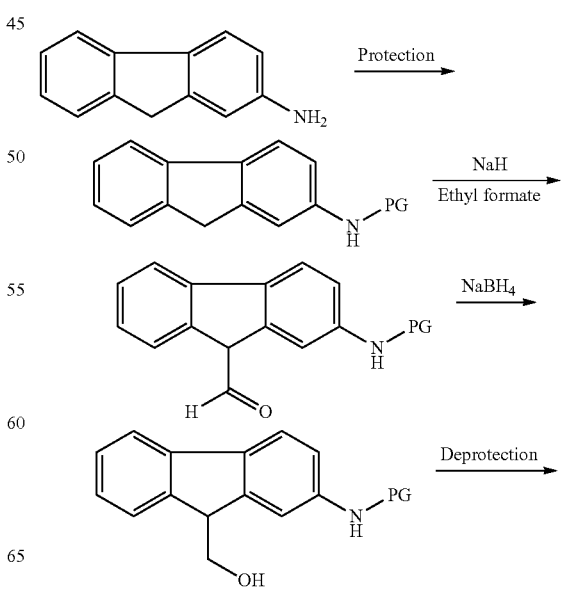

53
-continued

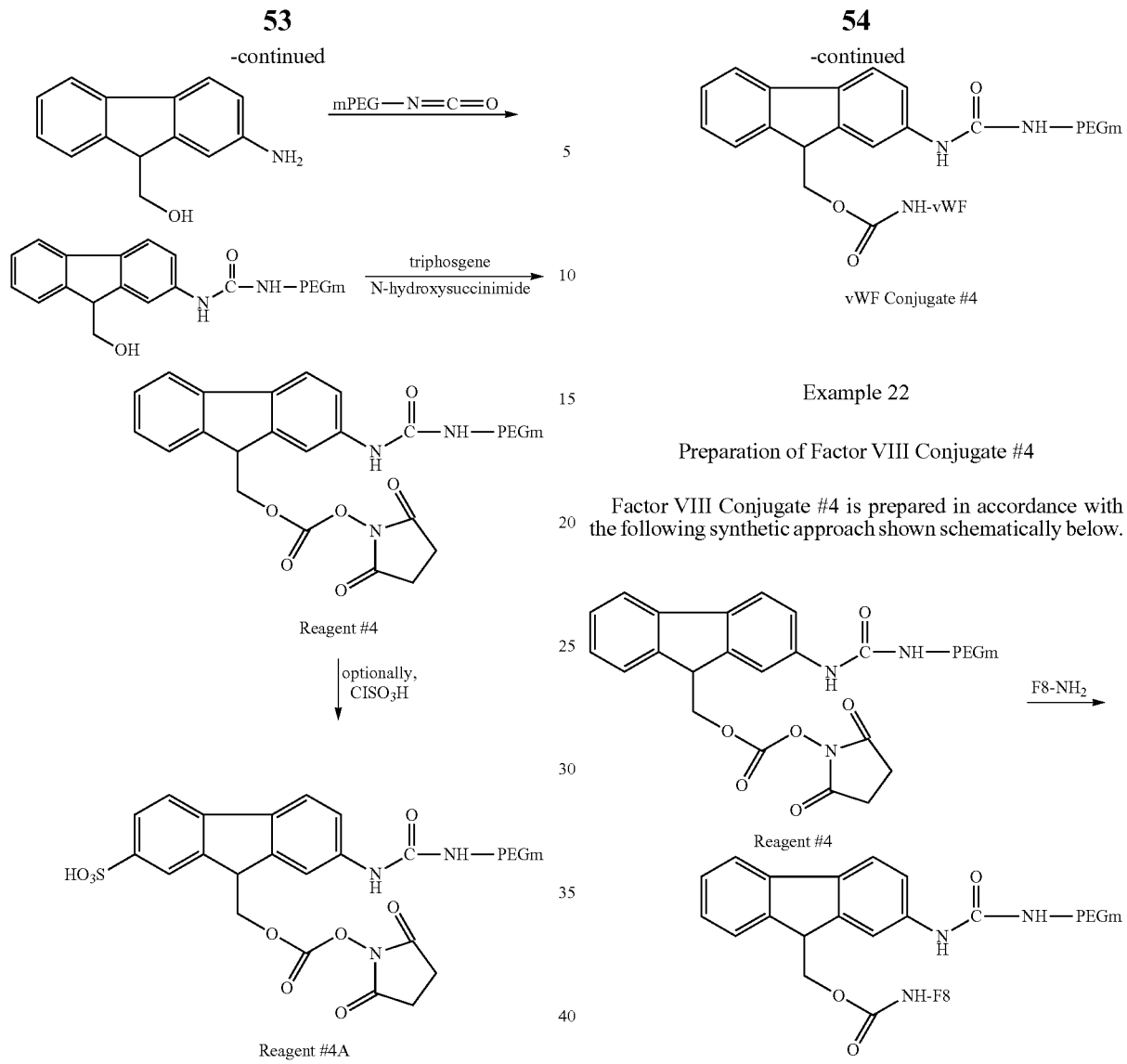

Reagent #4

Reagent #4A

Example 21

Preparation of von Willebrand Factor Conjugate #4 von Willebrand Factor Conjugate #4 is prepared in accordance with the following synthetic approach shown schematically below.

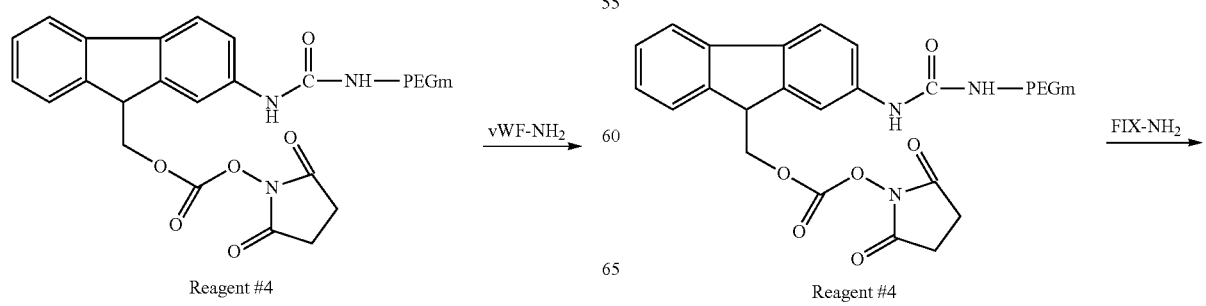

Reagent #4

54
-continued vWF Conjugate #4

Example 22

Preparation of Factor VIII Conjugate #4

Factor VIII Conjugate #4 is prepared in accordance with the following synthetic approach shown schematically below.

Reagent #4

F8 Conjugate #4

Example 23

Preparation of Factor IX Conjugate #4

Factor IX (FIX) Conjugate #4 is prepared in accordance with the following synthetic approach shown schematically below.

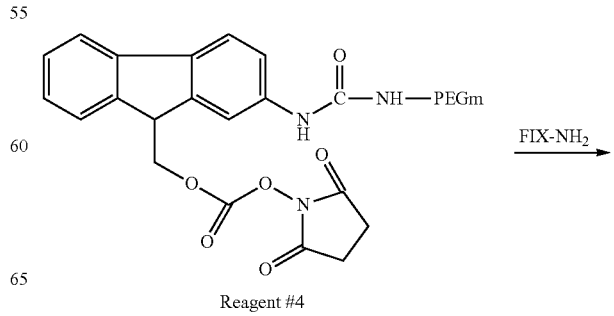

Reagent #4

-continued

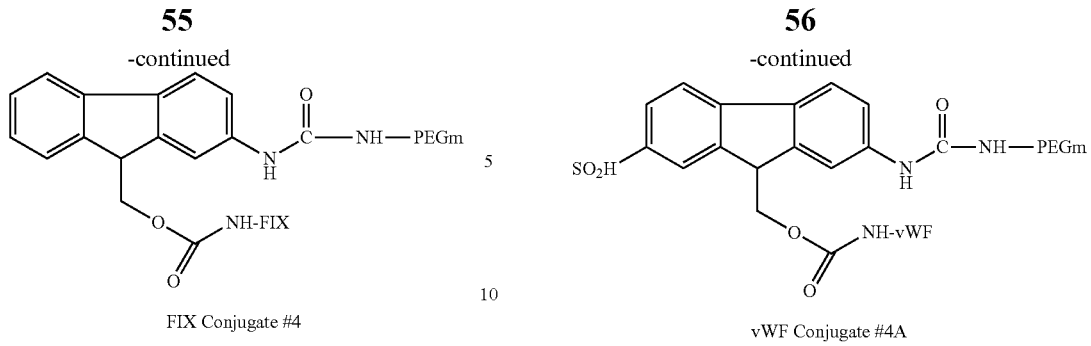

FIX Conjugate #4 vWF Conjugate #4A

Example 24

Preparation of Factor XI Conjugate #4

Factor XI (FXI) Conjugate #4 is prepared in accordance with the following synthetic approach shown schematically below.

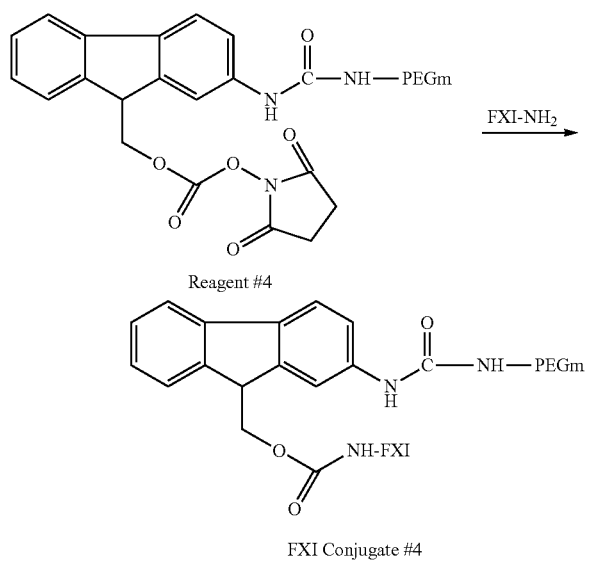

Example 25

Preparation of von Willebrand Factor Conjugate #4A von Willebrand Factor Conjugate #4A is prepared in accordance with the following synthetic approach schematically below.

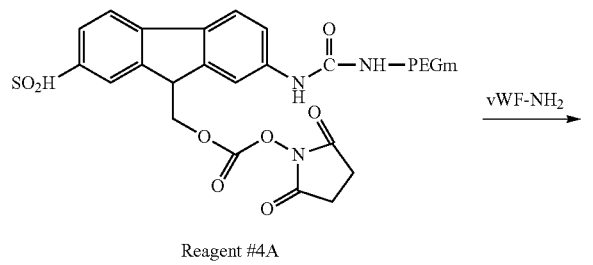

Example 26

Preparation of Factor VIII Conjugate #4A

Factor VIII Conjugate #4A is prepared in accordance with the following synthetic approach shown schematically below.

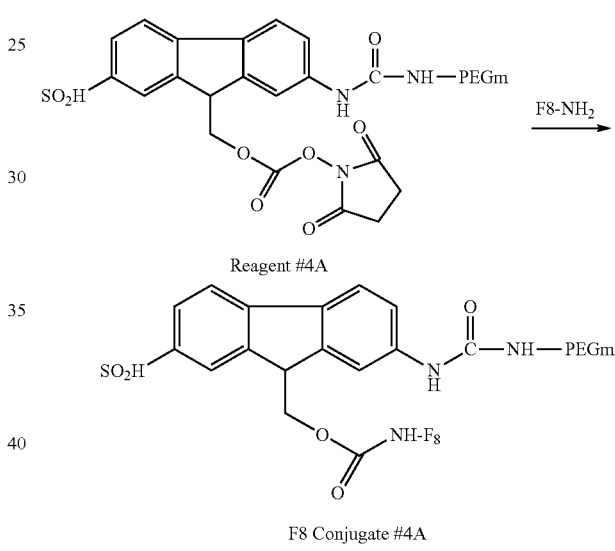

Example 27

Preparation of Factor IX Conjugate #4A

Factor IX (FIX) Conjugate #4A is prepared in accordance with the following synthetic approach shown schematically below.

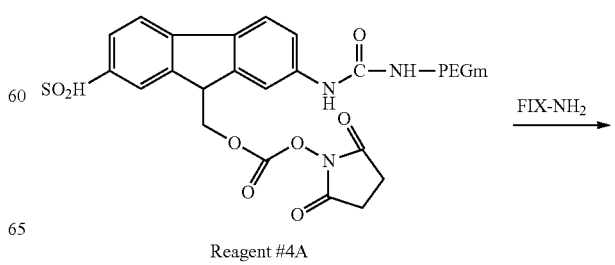

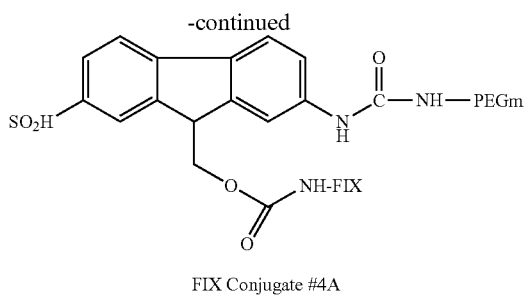

FIX Conjugate #4A

Example 28

Preparation of Factor XI Conjugate #4A

Factor XI (FXI) Conjugate #4A is prepared in accordance with the following synthetic approach shown schematically below.

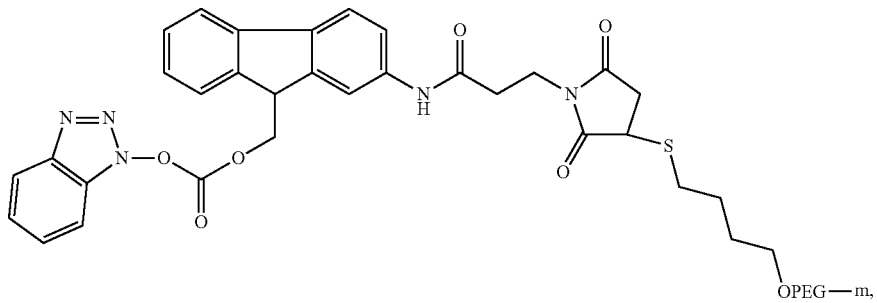

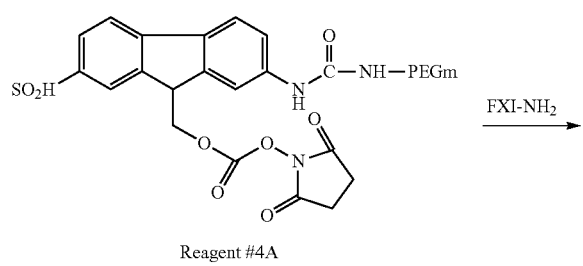

Reagent #4A

FXI Conjugate #4A

Example 29

Preparation of Factor VIII (FVIII) Conjugate (20 kDa)

FVIII protein solution (2.79 mg/mL) was quickly thawed (using a warm water bath at room temperature for five minutes) and, using a 1000 μL pipettor, approximately 1.1 mL of warmed FVIII protein solution was placed in a 5 mL low endotoxin cryotube. An aliquot of 0.43 mL of Milli-Q water was added to the FVIII solution to form a protein concentration of 2.0 mg/mL containing 3 mg of FVIII. A stir bar was added to the tube and the solution was allowed to mix at med-low speed on a stir plate. The 20K mPEG-SH-Mal-aminoFMOC-BTC, was removed from −20° C. and warmed to room temperature for one hour. A 63.5 molar ratio (relative to Factor VIII) of PEG (14.1 mg) was weighed out into a 2 mL microcentrifuge tube. The PEG was then resuspended in 188 μL of 2 mM HCl to form a 74.9 mg/mL PEG solution. The PEG was solubilized by alternating and centrifuging the microcentrifuge tube over a twenty second period.

Using a pipettor, the PEG solution was added to the FVIII protein solution dropwise over 1-20 seconds. The resulting mixture was maintained at room temperature (approximately 22° C.) for one hour. At the end of one hour, 18 μL of 1 M glycine solution was added to thereby form a glycine-containing PEGylation reaction mixture. A 100 μL sample was placed in a 500 μL microcentrifuge tube and then placed in a −80° C. freezer for further analysis.

To purify the conjugate within the glycine-containing PEGylation reaction mixture, the glycine-containing PEGylation reaction mixture was diluted 1:7 with purification buffer A [20 mM Histidine, 5 mM $CaCl_2$, 0.1% Tween 80, pH 6.5]. The conjugate was purified by cation exchange chromatography on an AKTA Prime System. The column used was a 1 mL HiTrap Q HP column (system and column were washed with 0.1 M NaOH and complete removal of NaOH was verified by testing for neutral or near neutral pH following washing with Milli-Q water or purification buffer). The PEG-FVIII diluted reaction mixture was loaded onto the column and the column was washed with 10 mL of purification buffer A at 1.0 mL/min. while collecting the flow through in 1 mL fractions. The following gradient was used with purification buffer B as 20 mM Histidine, 5 mM $CaCl_2$, 0.1% Tween 80, pH 6.5, 1 M NaCl: 0% of the starting buffer containing buffer B; a step to 50% of buffer B was held for 3 mL (the peak was collected in approximately 1 mL fractions and were stored on ice); a step to 100% of buffer B was used and held for 1 mL; and finally, a step back to 0% buffer B was used and held for 5 mL.

Protein determination was carried out by thawing 1×0.2 mL aliquot of purified conjugated sample and 100 µL/mL of Factor VIII. A standard curve with points at 0.25, 0.5, 0.75, and 1.0 mg/mL of Factor VIII was prepared. For each run (sample, standard, or purification buffer), 30 µL of the appropriate substance was placed in a clean 5 mL tube and 1.5 mL of Pierce Protein Assay Reagent (Pierce Biotechnology, Inc., Rockford Ill.) was added to the tube and was followed by mixing of the contents of the tube. After incubation for ten minutes at room temperature (22° C.), the contents of each tube were read using a spectrophotometer at 595 nm.

The purified conjugate sample was analyzed by SDS-PAGE by allowing a 3-8% Tris-Acetate gel (Invitrogen Corporation, Carlsbad Calif.) warming to room temperature, wherein a standard curve of PEG reagent in 2 mM HCl at concentrations of 0.001%, 0.01% and 0.1% (w/v) was made. The standard was prepared by placing 10 µL of HiMark molecular weight maker (Invitrogen Corporation, Carlsbad Calif.) into Lane 1. Purified conjugate sample or control (Factor VIII) (10 µL volume) were each individually diluted with 30 µL of 2 mM HCl, wherein 30 µL of each HCl diluted sample or control was combined with 10 µL of 4×LDS Sample Buffer (Invitrogen Corporation, Carlsbad Calif.), wherein 25 µL of the solution was then transferred to the designated well. Immediately, the get was placed in gel apparatus and was run for 60 minutes at 150 volts. Following completion of the run, the gel was removed from the gel apparatus and rinsed with deionized water. The gel was then stained with a barium iodine stain (performed by: adding 15 mL 0.1 M perchloric acid to the gel followed by a five minute incubation period; followed by addition to the gel of 5 mL of 5% barium chloride then 2 mL of iodine followed by a five minute incubation period) followed by rinsing with deionized water. Five minutes after the gel was rinsed with deionized water, the gel was analyzed with a Kodak Gel Logic Scanner system (Eastman Kodak Company, New Haven Conn.), wherein un-reacted PEG was identified. After scanning, any remaining water was poured off the gel and 50 mL of Pierce Imperial Stain (Pierce Biotechnology, Inc., Rockford Ill.) was added to the gel. Following incubation t room temperature for 30 minutes, the gel was rinsed with deionized water and allowed to stand for one hour in 200 mL of deionized water. During the hour period, several changes of water were completed. After the hour, the gel was analyzed with a Kodak Gel Logic Scanner system (Eastman Kodak Company, New Haven, Conn.). The SDS-PAGE analysis suggested that PEG was conjugated to Factor VIII.

Example 30

Preparation of von Willebrand Factor Conjugate #5 von Willebrand Factor Conjugate #5 is prepared in accordance with the following synthetic approach shown schematically below.

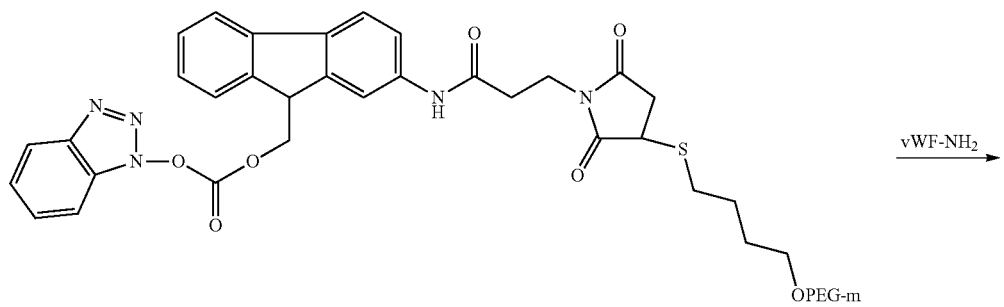

Reagent #5

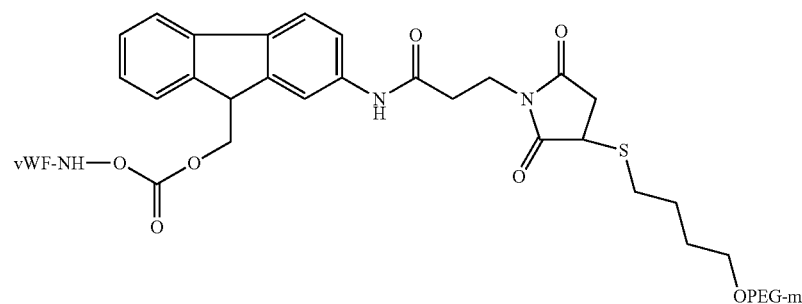

vWF Conjugate #5

What is claimed is:

1. A compound having the following structure:

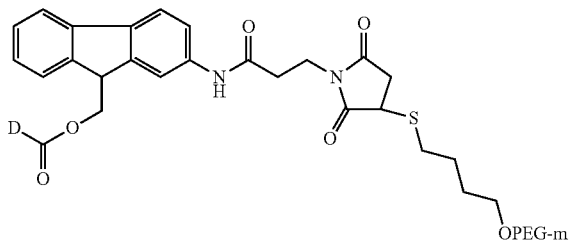

wherein:
- D is a residue of an active agent bearing at least one amino group; and;
- PEG-m is a methoxy end-capped poly(ethylene glycol), and further wherein the active agent is a coagulation factor having a molecular weight of greater than 100 kDa.

2. The compound of claim 1, wherein the coagulation factor is Factor VIII.

3. The compound of claim 2, wherein the coagulation factor is a recombinantly synthesized coagulation factor of human origin.

4. The compound of claim 1, wherein the poly(ethylene glycol) has a weight-average molecular weight of between 10,000 Daltons to 85,000 Daltons.

5. The compound of claim 4, wherein the poly(ethylene glycol) has a weight-average molecular weight of between 20,000 and 50,000 Daltons.

6. The compound of claim 1, wherein the poly(ethylene glycol) has between about 20 to 2000 monomeric repeats.

7. The compound of claim 6, wherein the poly(ethylene glycol) has between about 100 to 1000 monomeric repeats.

8. A composition comprising a compound of claim 1, and a pharmaceutically acceptable excipient.

9. A method of treatment comprising administering a composition of claim 8 to a subject in need thereof.

* * * * *

UNITED STATES PATENT AND TRADEMARK OFFICE
CERTIFICATE OF CORRECTION

| | | |
|---|---|---|
| PATENT NO. | : 8,575,102 B2 | Page 1 of 1 |
| APPLICATION NO. | : 13/057042 | |
| DATED | : November 5, 2013 | |
| INVENTOR(S) | : Culbertson et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 282 days.

Signed and Sealed this
Twelfth Day of May, 2015

Michelle K. Lee
*Director of the United States Patent and Trademark Office*